United States Patent
Bonutti et al.

(10) Patent No.: US 10,561,838 B2
(45) Date of Patent: Feb. 18, 2020

(54) SYSTEMS AND METHODS FOR DELIVERY OF THERAPEUTIC AGENTS

(71) Applicant: P Tech, LLC, Effingham, IL (US)

(72) Inventors: Peter M. Bonutti, Manalapan, FL (US); Justin E. Beyers, Effingham, IL (US); Tonya M. Bierman, Dieterich, IL (US)

(73) Assignee: P Tech, LLC, Effingham, IL (US)

( * ) Notice: Subject to any disclaimer, the term of this patent is extended or adjusted under 35 U.S.C. 154(b) by 356 days.

(21) Appl. No.: 15/449,252

(22) Filed: Mar. 3, 2017

(65) Prior Publication Data

US 2017/0252556 A1  Sep. 7, 2017

Related U.S. Application Data

(60) Provisional application No. 62/303,097, filed on Mar. 3, 2016.

(51) Int. Cl.
| | | |
|---|---|---|
| *A61N 1/30* | (2006.01) | |
| *A61M 37/00* | (2006.01) | |
| *A61N 1/04* | (2006.01) | |

(52) U.S. Cl.
CPC .............. *A61N 1/303* (2013.01); *A61M 37/00* (2013.01); *A61M 37/0092* (2013.01);
(Continued)

(58) Field of Classification Search
CPC .......... A61M 5/14248; A61M 5/14276; A61M 37/0015; A61M 31/002; A61M 37/0092; A61M 5/2448; A61M 37/00; A61M 35/00; A61M 5/1723; A61M 5/14244; A61M 5/158; A61M 5/172; A61N 1/30; A61N 1/0448; A61N 1/044; A61N 1/303; A61N 1/325; A61N 1/327; A61N 1/306; A61N 1/0428; A61N 1/0436; A61K 9/0009; A61K 9/0024; A61B 18/1492; A61B 5/14865; A61B 5/4839; A61F 9/0017
(Continued)

(56) References Cited

U.S. PATENT DOCUMENTS

| | | | |
|---|---|---|---|
| H0000516 H | * | 9/1988 | Lattin .................... A61N 1/303 604/20 |
| 5,310,404 A | | 5/1994 | Gyory et al. |

(Continued)

FOREIGN PATENT DOCUMENTS

WO     88/00846 A1     2/1988

OTHER PUBLICATIONS

International Search Report and Written Opinion for PCT/US2017/20725, dated Jun. 7, 2017, 9 pages.

*Primary Examiner* — Manuel A Mendez
(74) *Attorney, Agent, or Firm* — Stinson LLP

(57) ABSTRACT

An iontophoresis system includes a preloaded reservoir containing one or more doses of a therapeutic agent. As a result, the therapeutic agent does not have to be loaded into the reservoir prior to use. In such a system, the preloaded reservoir is generally disposable. Various components of the iontophoresis system can be combined with the reservoir in a disposable cartridge that is selectively connectable to other, reusable components of the iontophoresis system. In addition, the entire iontophoresis system can be formed from one or more disposable, one-time-use modules.

20 Claims, 17 Drawing Sheets

(52) U.S. Cl.
CPC ... *A61N 1/0428* (2013.01); *A61M 2037/0007* (2013.01); *A61M 2205/051* (2013.01); *A61M 2205/057* (2013.01); *A61M 2205/058* (2013.01); *A61M 2205/3306* (2013.01); *A61M 2205/3368* (2013.01); *A61M 2205/3584* (2013.01); *A61M 2205/36* (2013.01); *A61M 2205/502* (2013.01); *A61M 2205/52* (2013.01)

(58) Field of Classification Search
USPC .......................................................... 604/20
See application file for complete search history.

(56) References Cited

U.S. PATENT DOCUMENTS

| | | | |
|---|---|---|---|
| 5,362,308 A | 11/1994 | Chien et al. | |
| 5,830,175 A | 11/1998 | Flower | |
| 5,865,786 A | 2/1999 | Sibalis et al. | |
| 6,385,487 B1 | 5/2002 | Henley | |
| 2005/0015042 A1 | 1/2005 | Sun et al. | |
| 2010/0016781 A1 | 1/2010 | Nakayama et al. | |
| 2013/0345615 A1* | 12/2013 | Higuchi | A61N 1/303 604/20 |

* cited by examiner

SYSTEMS AND METHODS FOR DELIVERY OF THERAPEUTIC AGENTS

FIELD

The present disclosure generally relates to systems and methods for delivering therapeutic agents to a body portion of a patient and, more specifically, to methods and systems using electrical and/or acoustic energy to deliver therapeutic agents.

BACKGROUND

Various techniques can be used to cause a therapeutic agent to penetrate tissue. For example, injections are commonly used to deliver a therapeutic agent to a location in or below the skin. Other techniques such as iontophoresis and sonophoresis can also be used and may be less invasive and/or painful. Iontophoresis uses an electrical field to drive an ionic therapeutic agent into target tissue. Sonophoresis uses acoustic energy to increase the permeability of tissue and drive a therapeutic agent that is suspended in a glycerin coupling gel into the target tissue. Each of these techniques is most frequently used for the transdermal administration of topical therapeutic agents. Although iontophoresis and sonophoresis have certain benefits over injections, such as being less invasive and painful, they have not been widely adopted. One primary limitation of these techniques is the inability to ensure accurate dosing. With iontophoresis, a user must fill a reservoir with the required amount of therapeutic agent prior to use. Moreover, once the device is filled, conventional iontophoresis systems lack the capability to accurately determine how much of the therapeutic agent is being absorbed. Furthermore, certain tissues can lack sufficient permeability to adequately administer a complete dose. It is likewise difficult to accurately administer a dose of therapeutic agent using sonophoresis. A therapeutic agent is suspended in acoustic coupling gel, which cannot be fully absorbed into the skin. The residual coupling gel left on the skin retains an unknown quantity of suspended therapeutic agent, which makes it difficult to determine how much of the therapeutic agent is properly administered.

SUMMARY

In one aspect, an iontophoresis system includes a preloaded reservoir containing one or more doses of a therapeutic agent. As a result, the therapeutic agent does not have to be loaded into the reservoir prior to use. In such a system, the preloaded reservoir is generally disposable. Various components of the iontophoresis system can be combined with the reservoir in a disposable cartridge that is selectively connectable to other, reusable components of the iontophoresis system. In addition, the entire iontophoresis system can be formed from one or more disposable, one-time-use modules.

In another aspect, an iontophoresis system is configured so that an active electrode and an indifferent electrode generally oppose one another when the electrodes are mounted on the body of the patient. The indifferent electrode is thought to aid the active electrode in driving the charged therapeutic agent into the body portion to improve penetration.

In another aspect, an iontophoresis system includes active and indifferent electrodes, as well as an auxiliary device, configured to be selectively coupled to the body portion of a patient. In certain embodiments, the auxiliary device is thought to enhance penetration of a therapeutic agent into the body portion of the patient, as compared with using the active and indifferent electrodes alone. Examples of suitable auxiliary devices include a heater, a chiller, an acoustic energy generator, an abrader, a vibrator, etc. An auxiliary device and the active and indifferent electrodes can be operated by an automated control system that automatically controls the apparatuses to improve penetration and/or another therapeutic variable.

In another aspect, an iontophoresis system includes one or more sensors configured to detect one or more conditions related to the quantity of a therapeutic agent that is effectively absorbed by the patient. Sensors can provide signals to a suitable controller that uses a control routine to regulate the supply of electrical energy to active and indifferent electrodes of the iontophoresis system. For example, the controller can be configured to supply current to the electrodes until it determines based on the sensor signal(s) that a desired dose of the therapeutic agent has penetrated into the body portion. A controller can also use the sensor signals to control auxiliary devices that enhance delivery of the therapeutic agent to the patient.

In still another aspect, acoustic energy and a topical therapeutic agent are sequentially applied to a body portion of a patient. For example, in one embodiment, acoustic energy is applied before applying the therapeutic agent; and in another embodiment, acoustic energy is applied after applying the therapeutic agent. Such sequencing is thought to allow for more precise dosing of the therapeutic agent and/or improve the conditions for accurately monitoring the amount of therapeutic agent that is delivered. The therapeutic agent can be applied with or without the aid of iontophoresis.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Systems for delivering a therapeutic agent to a patient are described herein. In general, the systems use one or both of iontophoresis and sonophoresis to administer therapeutic agents to a patient. It is contemplated that the delivery systems described below are commonly used in the transdermal delivery of therapeutic agents to a body portion of a patient. That is, the systems are operative to deliver a therapeutic agent from a location outside the patient's skin into the skin or through the skin to an internal body part (e.g., muscle, internal organs, blood vessels, etc.). It will be understood, however, that these systems may also be used in invasive procedures, such as in a surgical setting, to cause a therapeutic agent to penetrate a location in a patient's tissue that is not accessible. As will be discussed in further detail below, the various delivery systems described herein can include user friendly features that improve dosing certainty in iontophoresis and sonophoresis administrations of a therapeutic agent.

Figure 1:
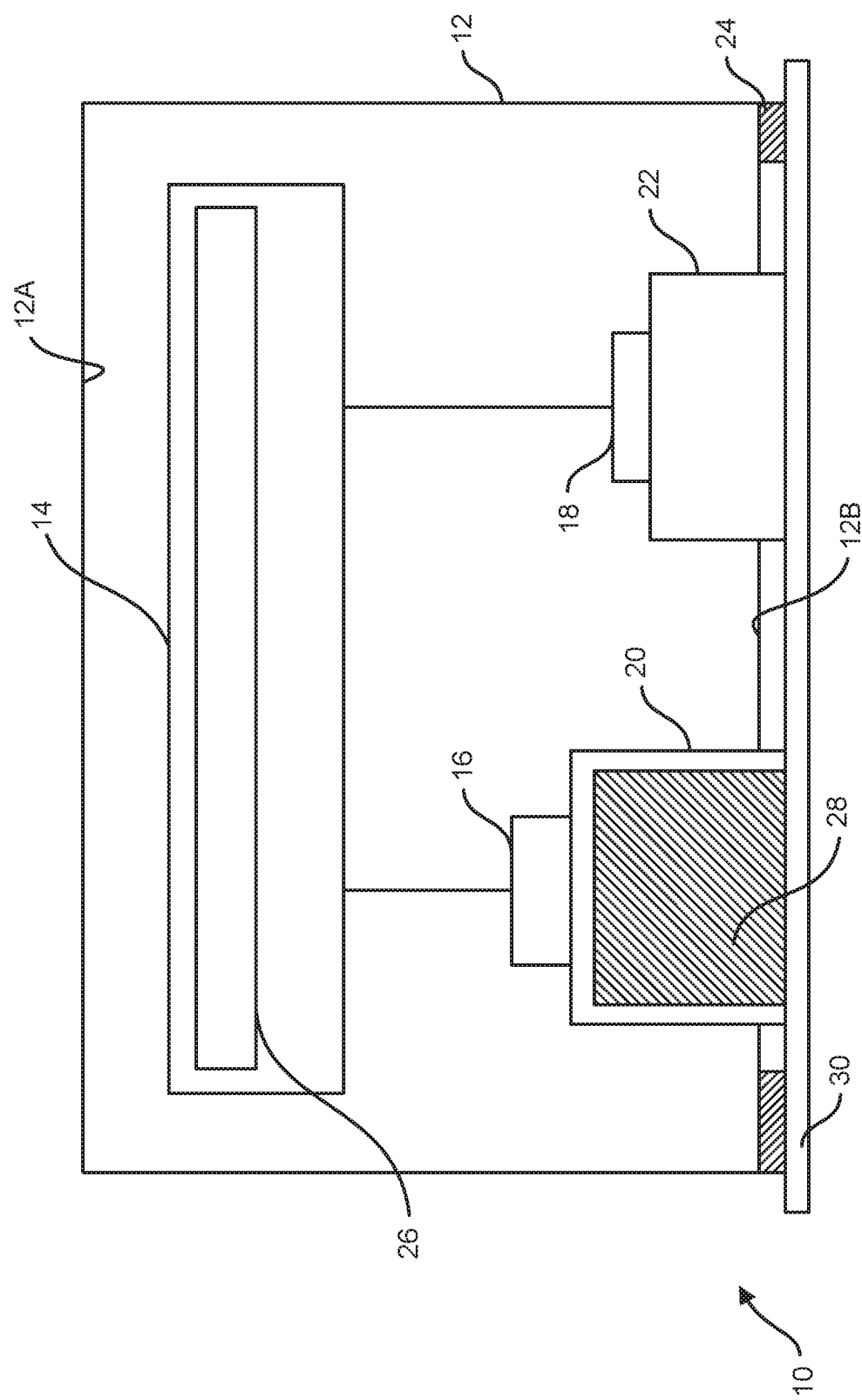
FIG. 1 is a schematic diagram of an iontophoresis system.

Referring to FIG. 1, an iontophoresis system is generally indicated at 10. As will be discussed in further detail below, the iontophoresis system 10 is suitably configured as an all-in-one and preloaded system for delivering a therapeutic agent to target tissue of a patient. Although the illustrated embodiment is an all-in-one and preloaded iontophoresis system, it will be understood that other types of therapeutic delivery systems can be used in other embodiments, and certain suitable embodiments of such other systems are described in further detail below. The iontophoresis system 10 includes a housing 12 (broadly, a support) that supports system electronics 14, an active electrode 16, an inactive electrode 18, electrical couplers 20, 22, and a surface mount 24. A suitable housing 12 can define one or more enclosures for receiving the various components of the iontophoresis system 10. In one or more embodiments, the housing 12 supports a control input (not shown) (e.g., a switch or a button, etc.) for selectively controlling one or more aspects of the electronics 14 and/or operating the iontophoresis system 10. In certain embodiments, the housing 12 supports the components of the iontophoresis system 10 in a fully operational configuration, such that the system can, for example, provide transdermal delivery of one or more therapeutic agents to target tissue in a patient using only the control inputs and without assembling the system in any manner. In one or more embodiments, system 10 may include more than one housing for one or more of the components of the system.

Although the illustrated housing 12 is generally rectangular in shape, housings of other shapes may also be used in various embodiments of the iontophoresis system 10. In the illustrated embodiment, the system electronics 14 are supported in a proximal end portion 12A of the housing 12 and the active and inactive electrodes 16, 18 are spaced apart toward a distal end portion 12B. The electrical couplers 20, 22 extend from the active and inactive electrodes 16, 18, respectively, through the distal end portion 12B of the housing 12 so that distal ends of the couplers are located outside the housing. The surface mount 24 is secured to the distal end 12B of the housing 12 for selectively mounting the iontophoresis system 10 on a body portion B of a patient (FIG. 2) (e.g., adjacent a patient's skin). A suitable housing 12 may be a one-piece body or a multiple piece assembly. Preferably, the housing 12 includes mounting structures for holding the components of the iontophoresis system 10 within and/or on the housing. A plastic injection molding process may be used to form the housing 12 in one or more suitable embodiments.

The electronics 14 include an electrical power supply 26 that may suitably comprise current control circuitry. The system electronics 14 can also include various other components such as one or more controllers, monitoring systems, communications hardware, displays, etc. In one or more embodiments, the power supply 26 is a monopolar power supply, for example, a direct current (DC) power supply, that has a positively charged terminal and a negatively charged terminal. Either of the positively or the negatively charged terminals can be connected to the active electrode 16, and the other of the terminals is connected to the indifferent electrode 18. In use, the power supply 26 creates a voltage difference at the electrodes 16, 18 and a closed circuit when the electrodes are each coupled to the same electrically conductive surface. As discussed below, the active electrode 16 typically functions to drive the therapeutic agent into the body portion B and the indifferent electrode functions to complete the circuit. In one or more embodiments, the power supply 26 is a disposable battery. For example, the power supply 26 can suitably be a film battery, which occupies minimal space in the housing 12. Such a battery may enable the housing 12 to have smaller exterior dimensions than other, larger batteries. In other embodiments, the power supply can comprise a capacitor. In one or more embodiments, the size of the power supply 26 is minimized by limiting the capacity to that required for delivering a single dose of a therapeutic agent using iontophoresis. In other embodiments, the capacity of the power supply 26 is limited to that required for delivering a predetermined number of doses that corresponds with an amount of therapeutic agent that is preloaded into the iontophoresis system 10. As discussed below, other iontophoresis systems may include reusable electronics, in which case a reusable battery and a corresponding charging circuit may be used for the power supply.

As discussed above, the active electrode 16 and the indifferent electrode 18 are operatively connected to the electronics 14 and power supply 26. The active electrode 16 can be an anode that is connected to the positively charged terminal of the power supply 16 or a cathode that is connected to the negatively charged terminal of the power supply, depending on the type of therapeutic agent that is being used. If a positively charged therapeutic agent is used, the active electrode 16 is the anode; and if a negatively charged therapeutic agent is used, the active electrode is the cathode. In reusable systems, the electronics can include a switch or an automatic controller configured to select either the anode or the cathode to be the active electrode, depending on whether the therapeutic agent is positively or negatively charged. The indifferent electrode 18 has the opposite charge of the active electrode 16.

Each of the electrodes 16, 18 is connected to a respective coupler 20, 22 for electrically coupling the electrode with a body portion B of a patient. Although the couplers 20, 22 are shown separately from the electrodes 26, 18 in the drawings, it will be understood that the electrodes can be constructed to integrally include a suitable coupler. In one or more embodiments, one or both of the electrical couplers 20, 22 comprise a skin contact for creating an electrical connection between a node of a circuit and a patient's skin. Other types of electrical contacts that electrically connect the electrodes 16, 18 with other bodily surfaces of a patient are also contemplated. For example, in one or more embodiments, the couplers 20, 22 are mucous membrane contacts suitable for electrical contact with a mucous membrane of a patient. Still other types of electrical contacts may also be used in other embodiments. When the couplers 20, 22 connect the electrodes 16, 18 to the body portion B, the power supply 26 functions as a voltage source and the body portion functions as a resistor in a closed circuit.

The active electrode coupler 20 includes a therapeutic agent reservoir 28. The reservoir 28 contains one or more ionic therapeutic agents. A patient or other user is not required to load the therapeutic agent into the reservoir 28 after manufacture of the system 10 before use. Thus, the illustrated all-in-one iontophoresis system 10 is "preloaded" with a therapeutic agent. Suitably, the reservoir 28 can be configured to prevent the preloaded therapeutic agent from escaping the reservoir prior to use. For example, the illustrated iontophoresis system 10 includes a cover comprising a release strip 30 (e.g., a tamper proof release strip 30, broadly tamper proof packaging) that covers the distal end portion 12B of the housing, including the open distal end or outlet of the reservoir 28. The release strip 30 can be removed from the outlet, but not necessarily from the device, prior to use to dispense the therapeutic agent from the reservoir during iontophoresis.

Figure 3:
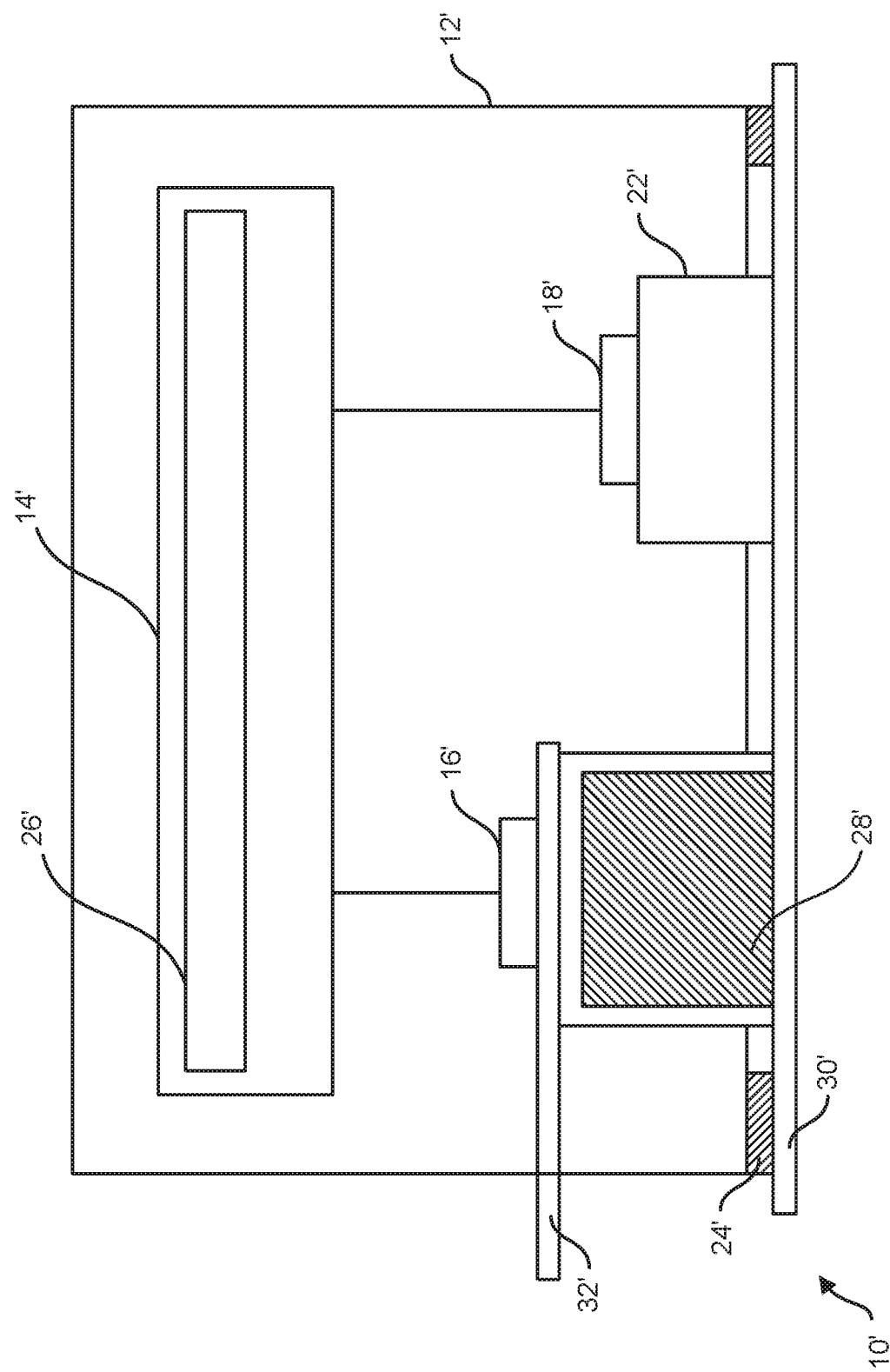
FIG. 3 is a schematic diagram of another embodiment of an iontophoresis system.

The reservoir 28 positions the therapeutic agent between the active electrode 16 and body portion B in use so that the active electrode can impart an electromotive force that drives the therapeutic agent into the body portion B. Before use, the reservoir 28 can, suitably, position the therapeutic agent in fluid communication with the active electrode 16 or in spaced apart relationship with the active electrode to prevent an undesired chemical reaction. During use, however, the active electrode 16 should be in electrical communication with the therapeutic agent in the reservoir 28. FIG. 3 shows another embodiment of the iontophoresis system 10' that includes a second release strip 32'. The release strip 32' is positioned between the active electrode 16' and the reservoir 28' prior to use to prevent fluid communication between the active electrode and therapeutic agent. Immediately before use, the release strip 32' is removed to connect the active electrode 16' with the therapeutic agent reservoir 28'. The release strip 32' could be used in combination with a spring or other force mechanism (not shown) that urges the electrode 16' and reservoir 28' into fluid communication after the release strip is removed.

Referring again to FIGS. 1 and 2, any suitable reservoir may be used to contain the therapeutic agent. For example, in one embodiment the reservoir 28 includes an open cell foam or an absorbent fabric (e.g., gauze) that is impregnated with the therapeutic agent. Suitably, the absorbent structure defines one or more flow passages that promote distal capillary flow of the therapeutic agent toward the body portion B in use. In other embodiments, the reservoir 28 defines an otherwise empty chamber that is at least partially filled with the therapeutic agent.

Suitably, the reservoir 28 can be configured to ensure local administration of the therapeutic agent. For example, the reservoir 28 can include a sealing structure (not shown) that extends circumferentially around an outlet opening. The sealing structure can be arranged so that the therapeutic agent passes through the sealing structure before being delivered to the body portion B. The sealing structure is configured to form a substantially liquid and/or fluid tight seal with the outer surface of the body portion B (e.g., the skin, a mucous membrane, etc.). The interior of the circumferential sealing structure thereby defines a local administration area. In use the therapeutic agent is driven into the body portion B at the local administration area and the circumferential seal prevents the therapeutic agent from flowing through the seal into contact with another area of the outer surface of the body portion. In one or more embodiments, the size of the local administration area can be adjusted to correspond with a particular treatment region. For example, the local administration could be sized to substantially correspond with a desired body part such as a biological lumen or organ (e.g., a vein, an artery, a specified muscle group, etc.). In use, the housing 12 is placed on the body portion B so that the local administration area substantially aligns with the desired body part and iontophoresis directs the therapeutic agent to the desired body part in a targeted manner.

Various therapeutic agents may be preloaded into the fluid reservoir 28. Suitably, a therapeutic agent may be a water soluble, ionic substance in an aqueous solution. Another therapeutic agent that is particularly well-suited to hyperhidrosis treatment is plain tap water. Therapeutic agents that are soluble in solvents other than water may also be used in other embodiments. For example, in one or more embodiments, the therapeutic agent is a dissolved component of a dimethyl sulfoxide (DMSO) solution. In some embodiments, the therapeutic agent, itself, may not be an ionic substance (e.g., a therapeutic agent comprising a lipid), but the solvent that carries that therapeutic agent is an ionic substance. It is believed that, as the electrical field generated by the iontophoresis system 10 drives the ionic solvent into the body portion B, the solvent can carry certain non-ionic therapeutic agents with it to administer the therapeutic agent to the patient. In still other embodiments, the therapeutic agent may be carried by a gel or paste. In suitable embodiments, the therapeutic agent is an active compound with a therapeutic effect (e.g., anesthetic, relaxant, anti-inflammatory, analgesia, blood flow stimulant, antiseptic, sweat suppressant, antibiotic, cosmetic, tissue reconstruction, antipuritic, etc.). Exemplary therapeutic agents include Acetic Acid, Calcium Chloride, Dexamethasone, Hydrocortisone, Hydrocortisone Prednisone, Iodine, Lidocaine, Magnesium Sulfate, Hyaluronidase, Salicylates, Tolazoline Hydrochloride, Zinc Oxide, chemotherapeutic agents, tap water, menthol, Diclofenac, etc.

In the illustrated embodiment, the mount 24 includes a temporary adhesive at the distal end portion 12B of the housing 12. The release strip 30 temporarily covers the adhesive 24 prior to use and can be removed to expose the adhesive. It will be understood that other mounts for mounting the iontophoresis system in operative engagement with a body portion B may also be used in other embodiments. For example, the housing 12 could be constructed so that, when the housing is pressed against a surface of a body portion B, the housing passively creates a vacuum in an interior chamber (e.g., like a suction cup) that holds the iontophoresis system 10 in operative connection with the body portion of the patient. The adhesive 24 is configured to secure the housing 12 to the body portion B so that the couplers 20, 22 are operatively connected to the outer surface of the body portion. For example, when the adhesive 24 properly secures the housing 12 to the body portion B, the couplers 20, 22 contact the body portion and the reservoir 28 is positioned in fluid communication with the body portion.

Figure 2:
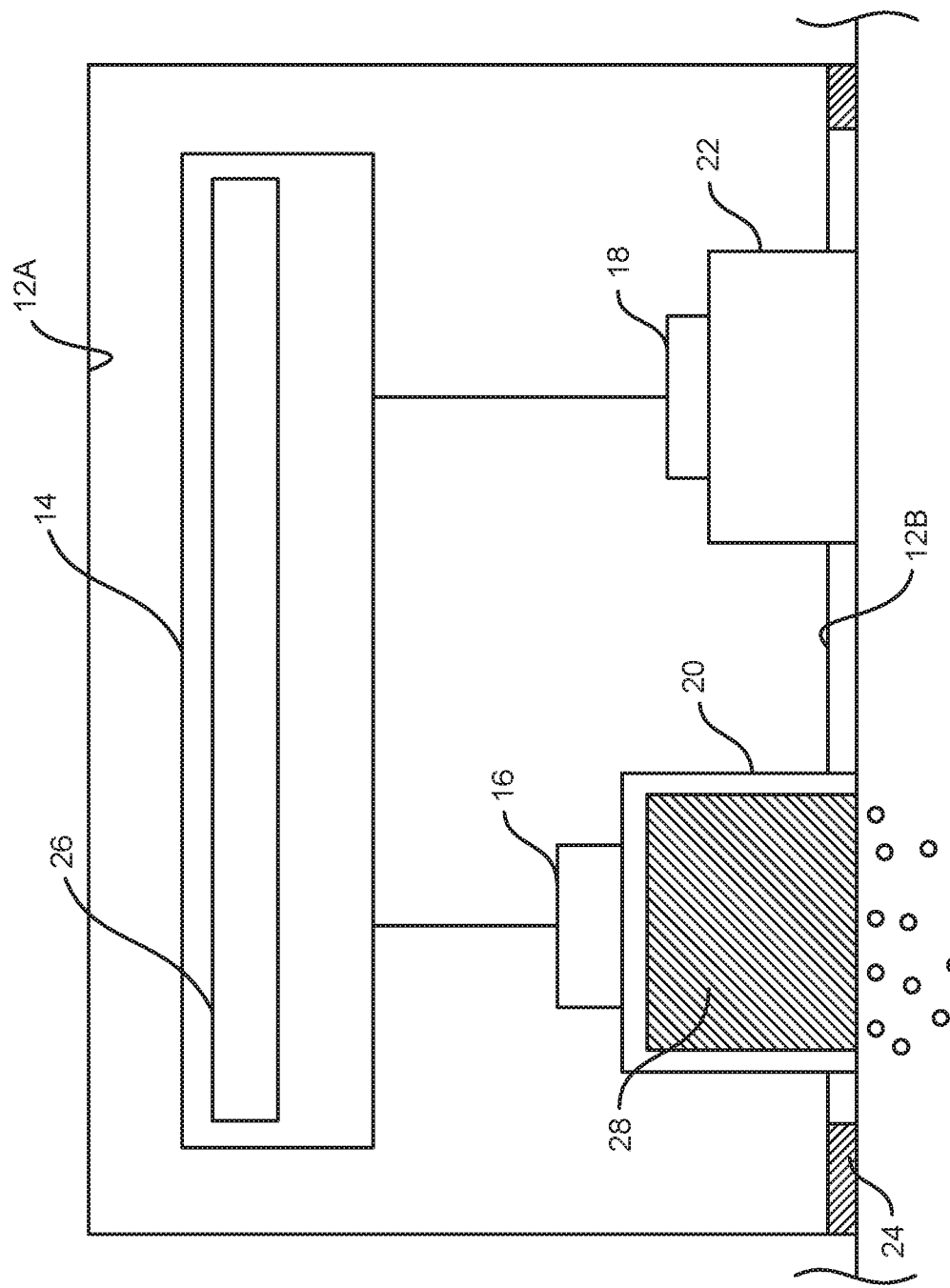
FIG. 2 is a schematic diagram of the iontophoresis system mounted on a body portion of a patient.

To use the iontophoresis system 10, a user removes the release strip 30 and secures the housing 12 to the body portion B of the patient using the mount 24. The user does not load the therapeutic agent into the iontophoresis system 10 prior to use, as the system is preloaded at manufacture. The mount 24 holds the iontophoresis system 10 so that the couplers 20, 22 electrically couple the active electrode 16 and the indifferent electrode 18 to the body portion B to create a closed circuit. The user can then operate the control input (not shown) on the housing 12 to activate the electronics 14. For example, by activating the iontophoresis system 10, the user can cause the power supply 26 to draw a current through the closed circuit. The power supply 26 will positively charge the active electrode 16 if the therapeutic agent is a positively charged ion or negatively charge the active electrode if the therapeutic agent is a negatively charged ion, thus repelling the therapeutic agent distally toward and into the body portion B. As shown in FIG. 2, the electrical repulsion causes the therapeutic agent to penetrate deeply into the tissue. The active electrode 16 may continue to repel the similarly charged ions of the therapeutic agent into the body portion B until a dose of the therapeutic agent has been delivered. If the iontophoresis system 10 is a single dose system, it can be removed and disposed of after the dose has been delivered. If the iontophoresis system 10 is a multi-dose system, it can optionally remain mounted on the patient or removed between administrations of doses.

In one or more embodiments, the electronics 14 include a controller that automatically controls the administration of the therapeutic agent to ensure the delivery of one or more complete doses. For example, the controller can automatically shut off the power supply 26 after a predetermined amount of time that is known to empirically correspond with a complete delivery of a dose of the therapeutic agent. In certain embodiments, this time period can be specifically configured for the subject/treatment, based on characteristics of the subject including skin type, treatment location, age, and/or therapeutic agent, etc. In some embodiments, the controller can be further configured to automatically administer multiple doses of the therapeutic agent by switching the power supply on after a predetermined time period after the administration of the first dose. The iontophoresis system 10 may include configuration inputs that allow the user to set the length of the predetermined time period between doses. In addition to using predetermined time periods to automatically control the dosing of therapeutic agents, other control variables may also be used as discussed in further detail below.

Thus, it can be seen that the all-in-one and preloaded iontophoresis system 10 is a user-friendly device. The iontophoresis system 10 may be particularly well-suited for self-administration of a therapeutic agent. Because the system 10 is preloaded with the desired dose of the therapeutic agent and the electronics 14 can be configured to automatically control delivery of a complete dose, the system minimizes the likelihood of user error.

Figure 4:
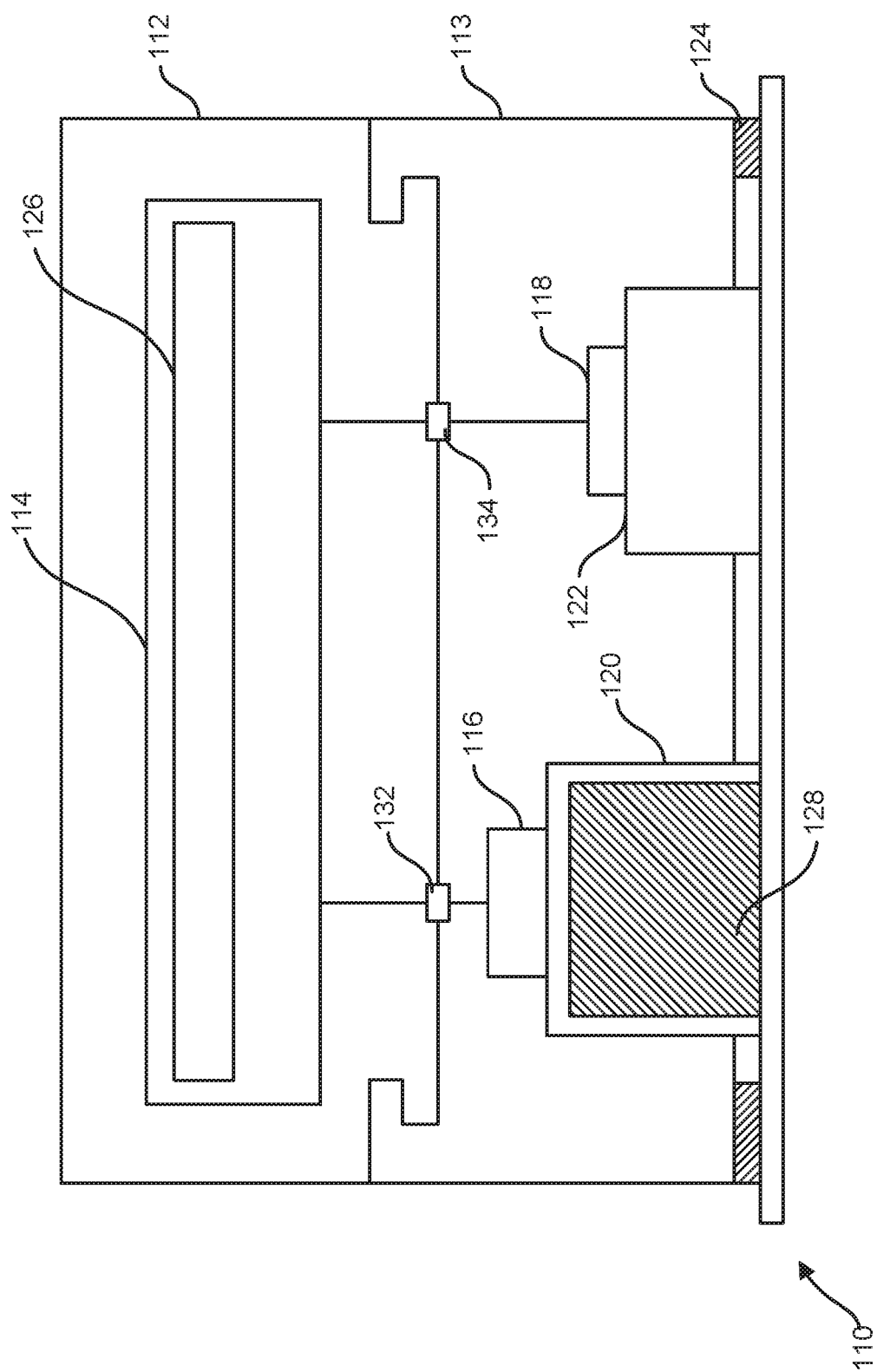
FIG. 4 is a schematic diagram of another embodiment of an iontophoresis system.

Referring to FIG. 4, another embodiment of a preloaded iontophoresis system is generally indicated at 110. Like the iontophoresis system 10, the iontophoresis system 110 includes electronics 114 comprising a power supply 126, an active electrode 116, an indifferent electrode 118, couplers 120, 122, a preloaded therapeutic agent reservoir 128, and a surface mount 124. Unlike the iontophoresis system 10, the iontophoresis system 110 includes first and second selectively separable modules 112, 113 that separately support certain components. The first module 112 is the electronics module that supports the system electronics 114, and the second module 113 is the administration module that supports the electrodes 116, 118, couplers 120, 122, reservoir 128, and surface mount 124. In the illustrated embodiment, the electronics module 112 is configured to be mounted on the administration module 113. Although FIG. 4 schematically illustrates a bayonet connection, any suitable mounting structure can be used to mount the electronics module 112 onto the administration module 113 (e.g., threaded connectors, mechanically interlocking structures, etc.). In addition, each of the modules 112, 113 includes respective electrical connectors 132, 134 for connecting the active electrode 116 and the indifferent electrode 118 to the terminals of the power supply 116. In certain embodiments the electronics module 112 is electrically connectable to the administration module 113 but is not structurally mountable thereupon. For example, lead wires can connect the electronics module 112 to the administration module 114 in certain embodiments. In one such embodiment, the administration module 113 is a bandage-type patch.

The electronics module 112 may be configured for reuse while the administration module 113 may be disposable and/or one-time use. For example, each administration module 113 may be preloaded with a single dose of therapeutic agent or another number of doses. The electronics module 112 can be connected to the administration module 113 and used to administer the therapeutic agent that is preloaded in the reservoir 128 as described above. Then, once the reservoir 128 is depleted, the user can remove the electronics module 112 from the administration module 113 and dispose of the administration module. When additional therapeutic agent is needed, the user can mount the electronics module 112 on a new administration module 113. Like the iontophoresis system 10, the iontophoresis system 110 uses features such as a preloaded reservoir 128 and system electronics 114 that provide dosing control in a user-friendly device for administering specified doses of therapeutic agent. But in addition, the iontophoresis system 110 is thought to be lower cost than the iontophoresis system 10 because the components of the electronics module 112 can be reused and only the administration module 113 needs to be replaced after each use. Moreover, the electronics module 112 can be constructed with more robust components that may have a higher cost because the module is configured for reuse.

Figure 5:
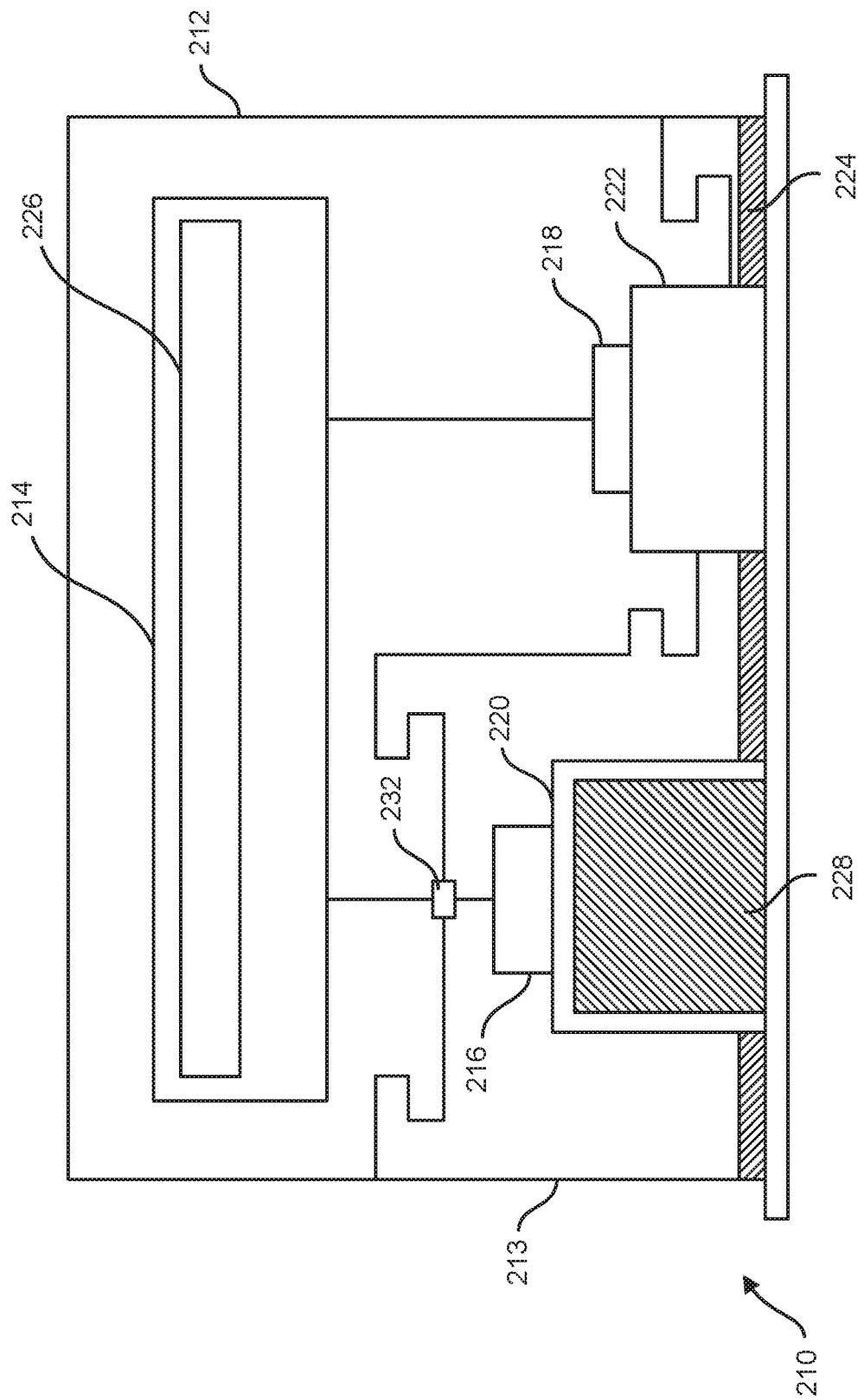
FIG. 5 is a schematic diagram of another embodiment of an iontophoresis system.

Referring to FIG. 5, another embodiment of a preloaded iontophoresis system is generally indicated at 210. Like the iontophoresis system 110, the iontophoresis system 210 includes an electronics module 212 and a selectively separable administration module 213. But unlike the iontophoresis system 110, the electronics module 212 of the iontophoresis system 210 includes the indifferent electrode 218 and the coupler 222, as well as the system electronics 214 and included power supply 226. Thus, the administration module 213 includes the active electrode 216, the coupler 220, and the preloaded therapeutic agent reservoir 228. An electrical connector 232 is configured to connect the active electrode 216 to the system electronics 214. The electronics module 212 can optionally be configured to be mounted on the administration module 213 or merely electrically connected through a wired connection. In a suitable embodiment, the electronics module 212 can be mounted on the administration module 213 so that the indifferent electrode coupler 222 aligns with the active electrode coupler 220 such that each of the couplers is operatively connected to the body portion B when the surface mount 224 mounts the iontophoresis system 210 on the body portion. In one or more embodiments, the administration module 213 is disposable and the electronics module 212 is reusable. As compared with the iontophoresis system 110, the iontophoresis system 210 may have an even lower cost because more of the components are reusable.

Figure 6:
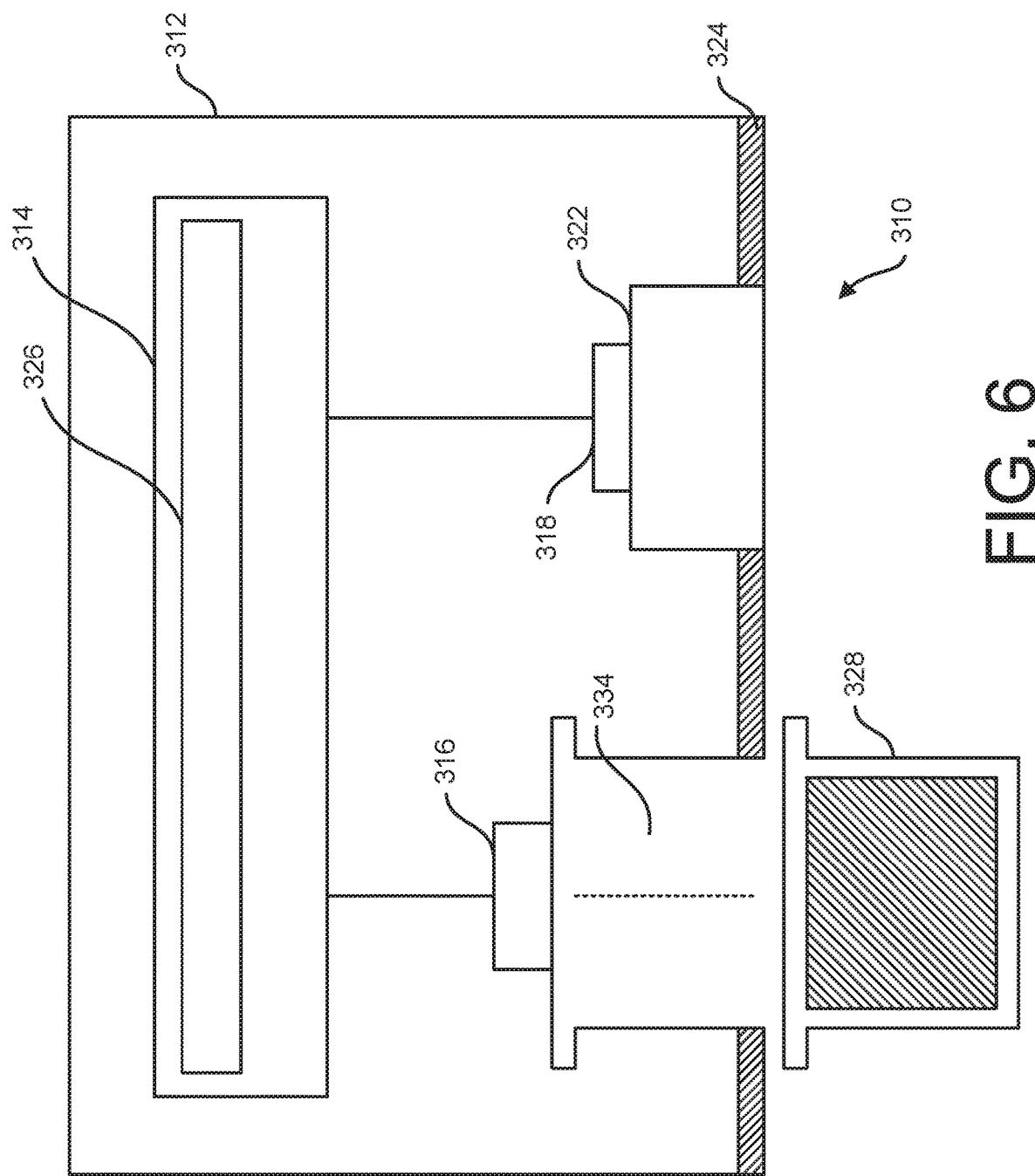
FIG. 6 is a schematic diagram of another embodiment of an iontophoresis system.

Referring to FIG. 6, in another embodiment, an iontophoresis system 310 maximizes the number of reusable components. The iontophoresis system 310 includes a housing 312 that supports system electronics 314, a power supply 326, an active electrode 316, an indifferent electrode 318, an indifferent electrode coupler 322, and a surface mount 324. The housing 312 defines a cavity 334 for receiving and operatively positioning a disposable, preloaded therapeutic agent cartridge 328. The therapeutic agent cartridge 328 is preloaded with one or more doses of therapeutic agent. The cartridge 334 can include one or more removable structures (e.g., lids, release strips, wrappers, etc.) that contain the therapeutic agent in the cartridge 334 prior to use. Before the cartridge 328 is loaded into the cavity 334, these removable structures are removed so that the therapeutic agent can be delivered from the cartridge to the body portion B using iontophoresis. In one or more embodiments, the replaceable cartridge 328 functions as a coupler for electrically coupling the active electrode 316 with the body portion B of the patient. After the therapeutic agent in one cartridge 328 has been delivered, a user can dispose of the spent cartridge and refill the cavity 334 with a new cartridge. Although the illustrated embodiment, shows the replaceable cartridge 328 being usable with an all-in-one iontophoresis system it will be understood that the replaceable cartridge could be used with a modular iontophoresis system with separate reusable electronics and administration modules. In one or more suitable embodiments the surface mount 324 is reusable and/or replaceable after each use. For example, replaceable adhesive strips can be applied to the distal end of the housing 312 each time it is mounted on the body portion B. An exemplary reusable surface mount is also discussed in further detail below.

Figure 7:
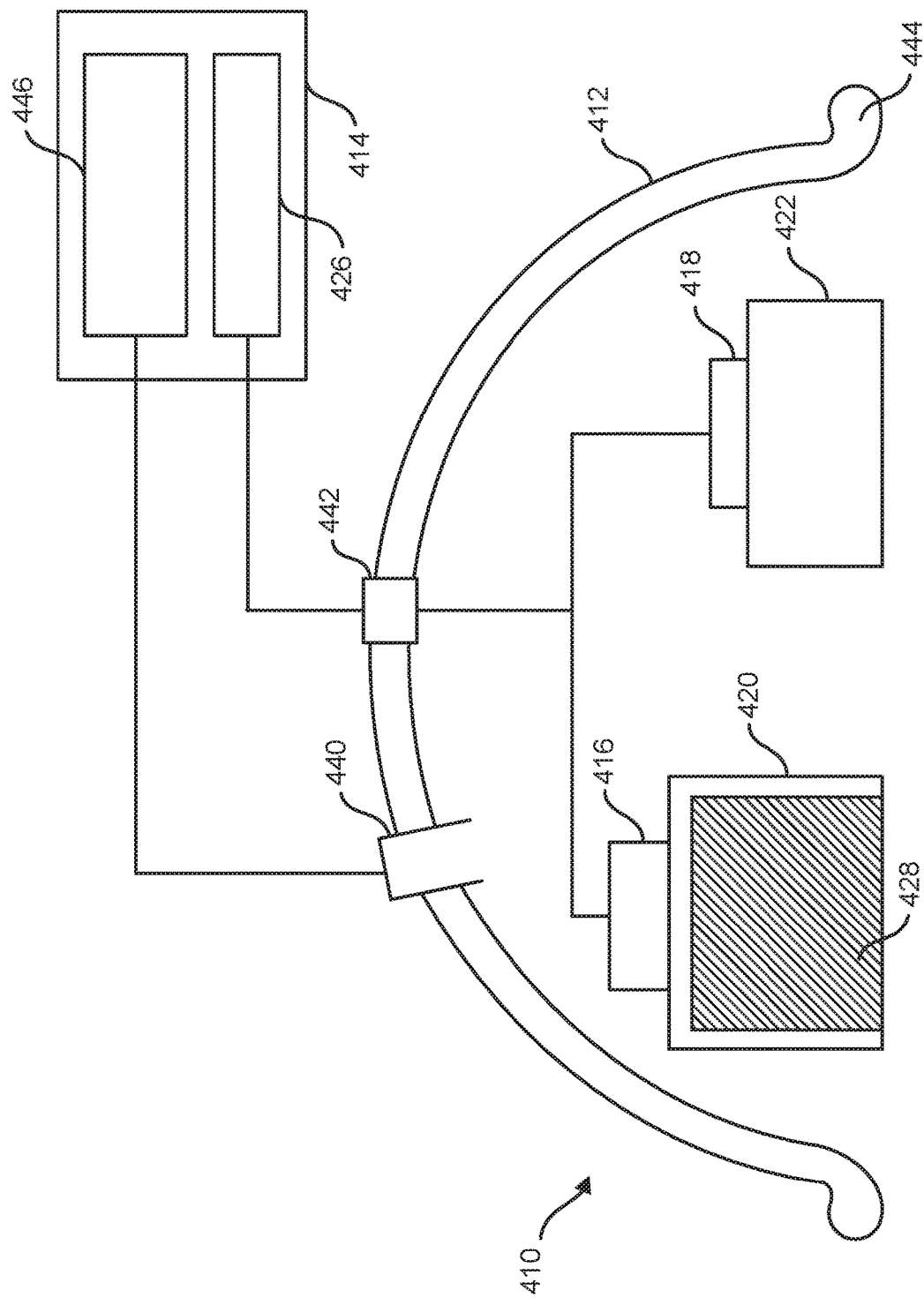
FIG. 7 is a schematic diagram of another embodiment of an iontophoresis system.
Figure 8:
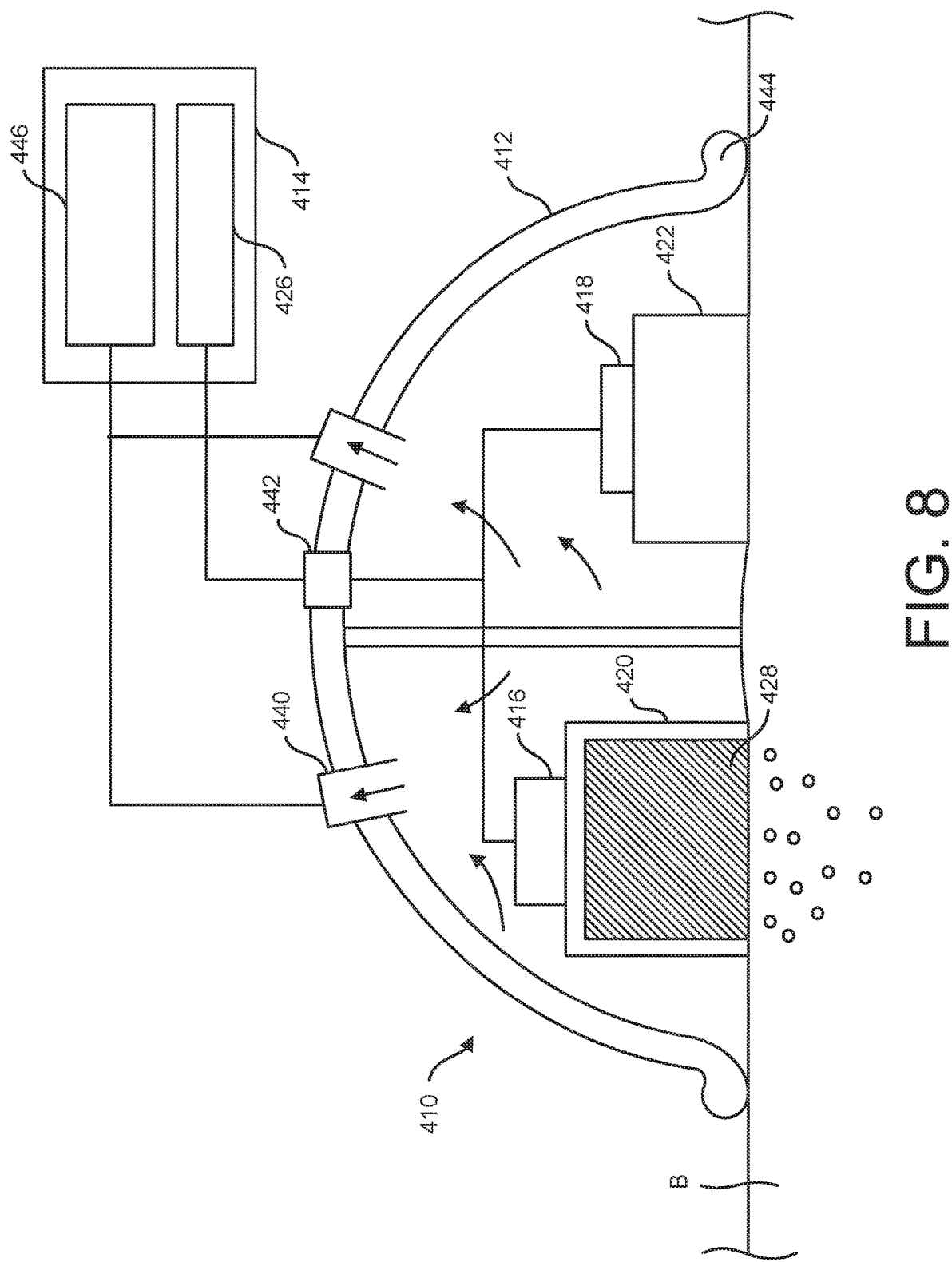
FIG. 8 is a schematic diagram of the iontophoresis system of FIG. 7 mounted on the body portion.

Referring to FIGS. 7 and 8, another embodiment of an iontophoresis system is generally indicated at 410. Like the iontophoresis system 10, the iontophoresis system 410 includes a housing 412 that supports an active electrode 416, an indifferent electrode 418, electrode couplers 420, 422, and a fluid reservoir 428, which may be preloaded or fillable. Unlike the housing 12, the housing 412 is generally dome-shaped, but the housing could have other shapes without departing from the scope of the invention. For example, rather than a rigid housing 412, the active electrode 416, indifferent electrode 418, couplers 420, 422, and fluid reservoir 428 could be supported by one or more flexible patches comprising fluid impermeable backing(s) configured for engaging the body portion B and forming a fluid-tight seal therewith. An air fitting 440 and electronics connector 442 extend through a proximal wall of the housing 412 (or fluid impermeable backing). A distal end portion of the housing 412 defines a circumferential rim 444 that is configured for continuous circumferential engagement with the body portion B in use. Where a flexible patch or patches are used in lieu of the housing 412, the patches can comprise an adhesive or other sealing structure that extends circumferentially around one or more of the components of the iontophoresis system 410 that are configured for operative engagement with the body portion B. In addition, the adhesives could be positioned on a semipermeable membrane extending over the reservoir 428. It is understood that a semipermeable membrane supporting an adhesive could be used with any of the iontophoresis systems discussed herein.

In the illustrated embodiment, the system electronics 414 are located remote from the housing 412 in a separate module. However, all or some of the system electronics could be supported by the housing 412 in other embodiments. As above, the system electronics include a power supply 426. The opposite terminals of the power supply 426 are connected to the connector 442 in the proximal wall of the housing 412, and internal wires carry the current from the connector to the active electrode 416 and the indifferent electrode 418, respectively. In addition to the power supply 426, the system electronics 414 includes a vacuum 446 that is operatively connected to the air fitting 440 to apply negative pressure to the interior of the housing 412. Although the vacuum 446 is located remote from the housing 412 in the illustrated embodiment, it can also be mounted on or within the housing in other embodiments. When a fluid impermeable patch or patches are used in lieu of the housing 412, the air fitting 440 can operatively connect the vacuum 446 to a distal side of the fluid impermeable backing to apply negative pressure to a space between the backing and the body portion of the patient.

In use, the external system electronics 414 and vacuum 446 are connected to the electrical connector 442 and air fitting 440, respectively. The user also places the housing 412 on the body portion B so that the rim 444 contacts the body portion around its entire circumference to form an airtight seal. If a patch were used instead, the user would place the patch so that a circumferential sealing structure (e.g., an adhesive seal) forms an airtight seal around the space between the body portion B and fluid impermeable backing. Preferably, the couplers 420, 422 are positioned within the housing 412 or on the fluid impermeable backing so that, when the housing or patch is properly placed on the body portion B, the couplers contact the body portion to electrically couple the electrodes 416, 418 and the body portion. Moreover, proper position of the housing 412 or fluid impermeable backing likewise positions the fluid reservoir 428 in fluid communication with the body portion B. With the housing 412 or patch(es) in the proper position, the user activates the system electronics 414. In a suitable embodiment, the system electronics 414 automatically causes the vacuum 446 to draw air through the air fitting 440 before activating the power supply 426 to begin iontophoresis. As shown in FIG. 8, as the vacuum 446 draws in air and negative pressure in the interior of the housing 412 increases, the housing is pulled tighter against the body portion B. When using the housing 412, the negative pressure in the interior eventually reaches a level that secures the housing to the body portion B without any additional holding force. In one embodiment, the system electronics 141 determine when sufficient vacuum pressure is established by monitoring an impedance of the body portion B. This can also be true when using the flexible patch(es), or the flexible patch(es) can be held against the body portion B using a mounting structure such as an adhesive. At this point the system electronics (either automatically or at the direction of the user) turns on the power supply 426 to begin iontophoresis. Suitably, the electronics 414 can include a controller that is configured to determine when the negative pressure in the housing interior is sufficient to mount the iontophoresis system 410 on the body portion (e.g., using a sensor) and to prevent the power supply from supplying current to the electrodes 416, 418 until that time. The reservoir 420 can include a sealing structure at the distal end for forming a sealed interface with the subject. The sealing structure can extend along the rim of the reservoir 420 around an opening or permeable membrane through which the therapeutic agent is discharged from the reservoir in use. The sealing structure inhibits therapeutic agent from flowing along the surface of the body portion of the subject without penetrating into the tissue to prevent the therapeutic agent from short-circuiting the current flow by forming a direct electrical pathway along the surface of the body portion between the active and indifferent electrodes 416, 418.

The iontophoresis system 410 using the housing 412 is particularly well suited to administering the therapeutic agent to a body portion B that has a mucous membrane. It is difficult to secure an administration module of an iontophoresis system to a mucous membrane using an adhesive mount. However, the above-described negative pressure mount is not affected by the moisture of the mucous membrane. Moreover, the use of negative pressure draws the body portion proximally into the interior of the housing 412 to create closer and more secure contact with the couplers 420, 422.

The iontophoresis system 410 may also be used in a wound treatment therapy, such as a therapy for the treatment of diabetic ulcers or other chronic wounds. In these embodiments, the housing or patch is placed over a wound (e.g., ulcer) so that the fluid reservoir is fluidly coupled with the wound and the housing or patch seals against the body portion B to define a sealed space between the housing or patch and the body portion B. The vacuum 446 draws a negative pressure in the space, which applies negative pressure therapy to the wound. Then, while the wound is being treated with negative pressure therapy, a suitable therapeutic agent is delivered to the wound using iontophoresis. Certain therapeutic agents that are thought to be suitable for wound treatment include saline, antibiotics, antimicrobials, retapamulin, hydrogels, hydrocolloids, alginates, collagenase, etc. Thus, using the iontophoresis system 410, iontophoresis may be combined with negative pressure wound treatment to enhance treatment of the wound.

Figure 9:
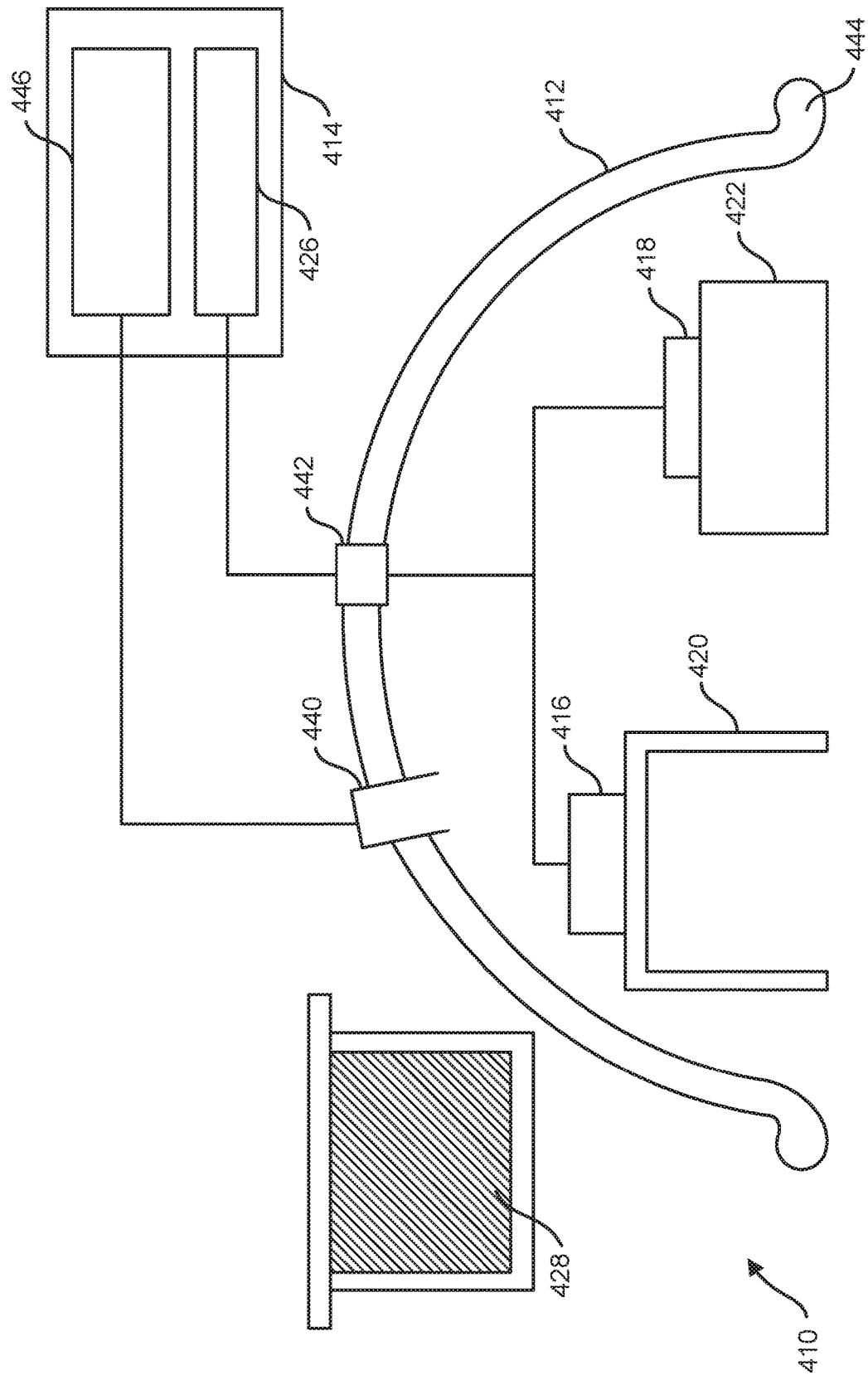
FIG. 9 is a schematic diagram of another embodiment of an iontophoresis system.

As shown in FIG. 9, in certain embodiments, the iontophoresis system 410 can be configured so that the reservoir 428 is a disposable cartridge containing the therapeutic agent, and the housing 412 is configured to operatively mount the disposable cartridge for dispensing the therapeutic agent using iontophoresis. In addition, the iontophoresis system 410 can likewise be configured as an all-in-one preloaded iontophoresis system or preloaded administration module of an iontophoresis system in other embodiments. For example, the flexible patches discussed above may be disposable administration modules that are preloaded with one or more doses of a therapeutic agent.

Figure 10:
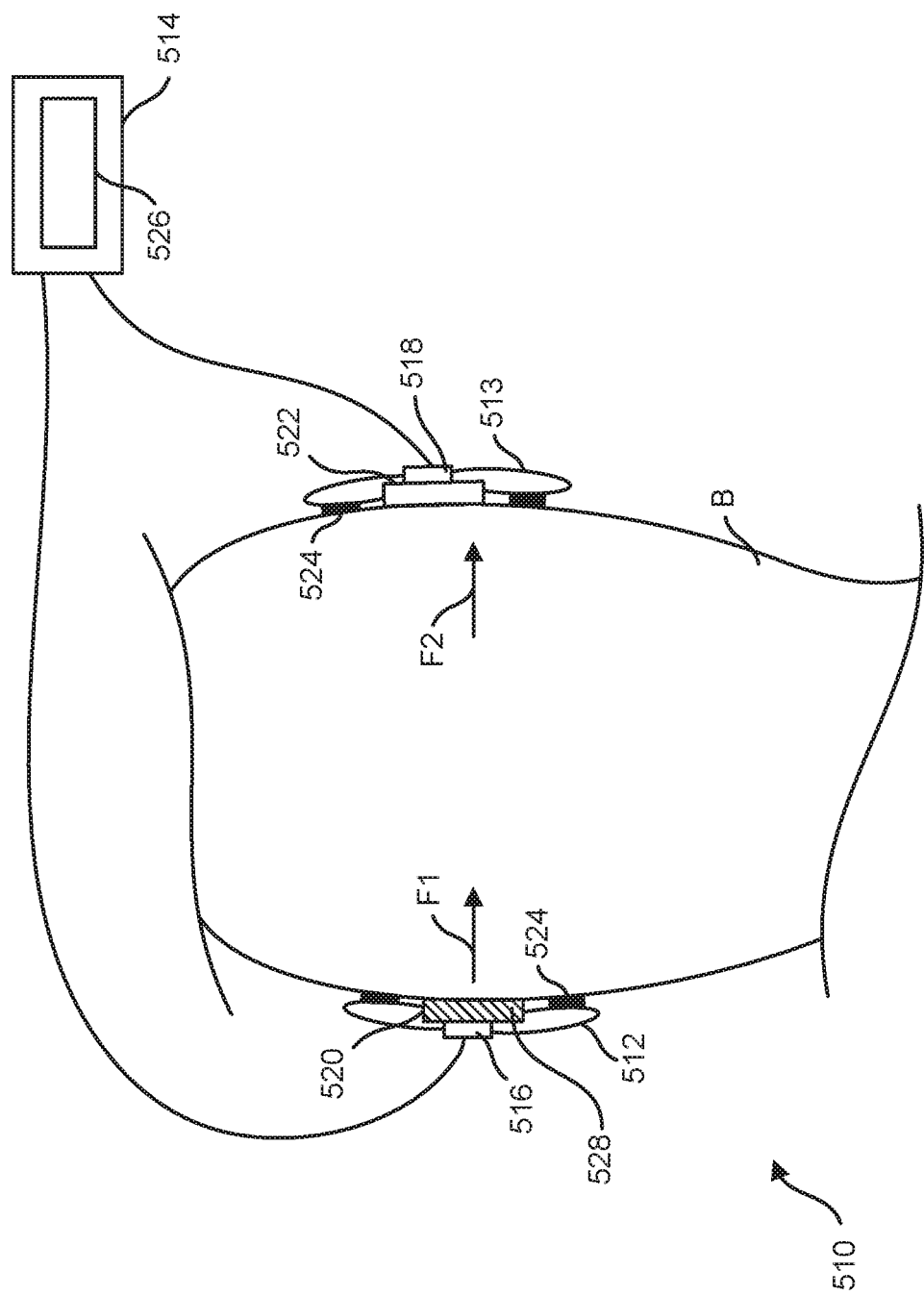
FIG. 10 is a schematic diagram of another embodiment of an iontophoresis system mounted on the body portion.

Referring to FIG. 10, another embodiment of an iontophoresis system is generally indicated at 510. The iontophoresis system 510 includes an active electrode 516, an indifferent electrode 518, and respective couplers 520, 522. External system electronics 514 include a power supply 526 and wires that connect the power supply to the electrodes 516, 518. Each of the electrodes 516 and 518 and its respective coupler 520, 522 is mounted on a separate patch 512, 513. The patches 512, 513 each include an adhesive strip 524 for operatively mounting the patches on a body portion B of the patient. In the illustrated embodiment, the patches 512, 514 are separable to allow each of the electrodes 516, 518 to be operatively connected to an opposing surface of the body portion B. In one or more embodiments, the patch 512 includes a reservoir 528 that is preloaded with one or more doses of a therapeutic agent.

In certain methods of using the iontophoresis system 510, the patches 512, 513 are operatively mounted on the body portion B so that the indifferent electrode 518 opposes the active electrode 516. For example, in one or more embodiments, the patches 512, 513 are mounted at diametrically opposed positions on the body portion B. The opposing relationship is thought to improve penetration of the therapeutic agent into the body portion B by utilizing the attractive forces of the charged indifferent electrode 518, as well as the repulsive forces of the oppositely charged active electrode 516. For example, as shown in FIG. 10, the active electrode 516 imparts a repulsive electromotive force F1 upon the therapeutic agent, which has the same charge as the active electrode. In addition, the indifferent electrode 518, which has an opposite charge, imparts an electromotive force F2 upon the therapeutic agent that tends to draw the therapeutic agent toward the indifferent electrode. The electromotive forces F1 and F2 are thought to act in combination upon the ionic therapeutic agent to drive the therapeutic agent further into the body portion B than the active electrode 514 acting alone, thus providing more confidence in complete dosing.

Figure 11:
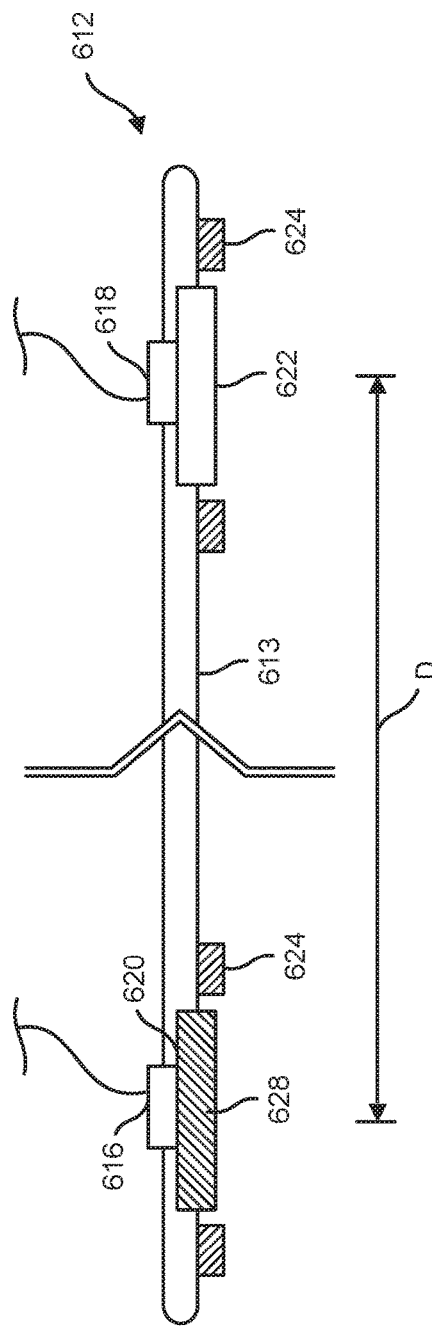
FIG. 11 is a cross section of another embodiment of an iontophoresis system illustrated schematically.
Figure 12:
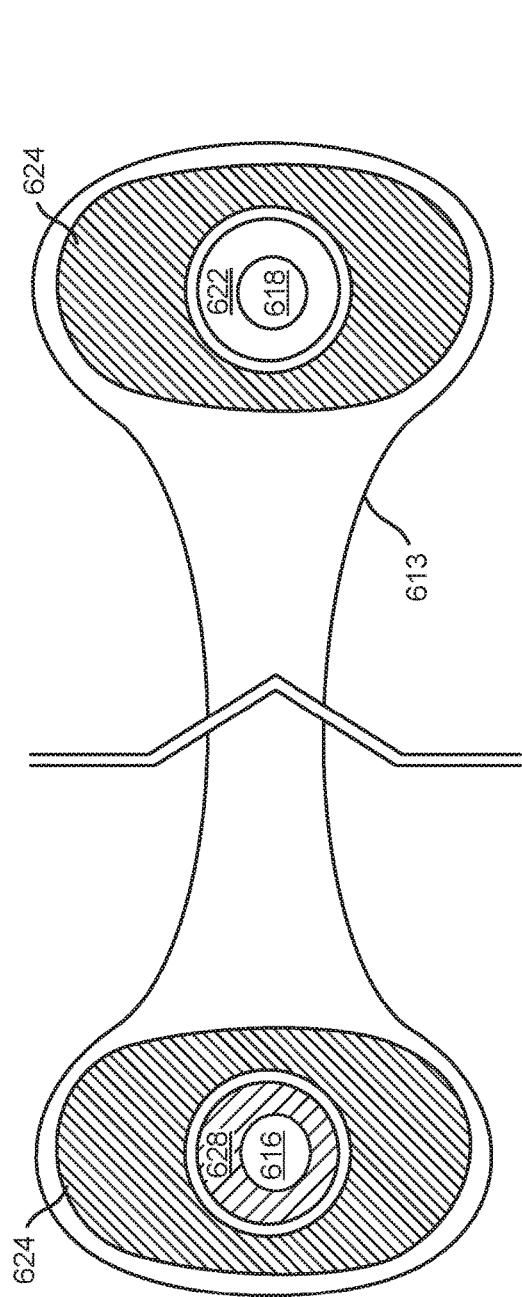
FIG. 12 is a plan view of the iontophoresis system of FIG. 11 illustrated schematically.

Referring to FIGS. 11 and 12, an iontophoresis patch is generally indicated at 612. The iontophoresis patch 612 is suitably configured to be connected to an external power supply (not shown). The iontophoresis patch 612 includes a one-piece base 613 that has a first end portion that supports an active electrode 616 and a coupler 620 and a second end portion that supports an indifferent electrode 618 and a coupler 522. Adhesive mounts 624 extend around each of the couplers 620, 266 for securing respective end portions of the patch 612 to a body portion B. The iontophoresis patch 612 further includes a reservoir 628 that can be pre-loaded with a therapeutic agent or filled with a therapeutic agent by a user.

The base 613 of the patch 612 includes an elongate central portion that extends between the first and second end portions. As a result, the active and indifferent electrodes 614, 616 are spaced apart by a distance D. In one or more embodiments, the distance D is between about 40% and about 60% (e.g., about 50%) of a circumference of a body portion B. Thus, when the patch 612 is wrapped circumferentially around the body portion B and mounted thereupon, the active and indifferent electrodes 616, 618 generally oppose one another to enhance penetration of the therapeutic agent into the body portion.

Figure 13:
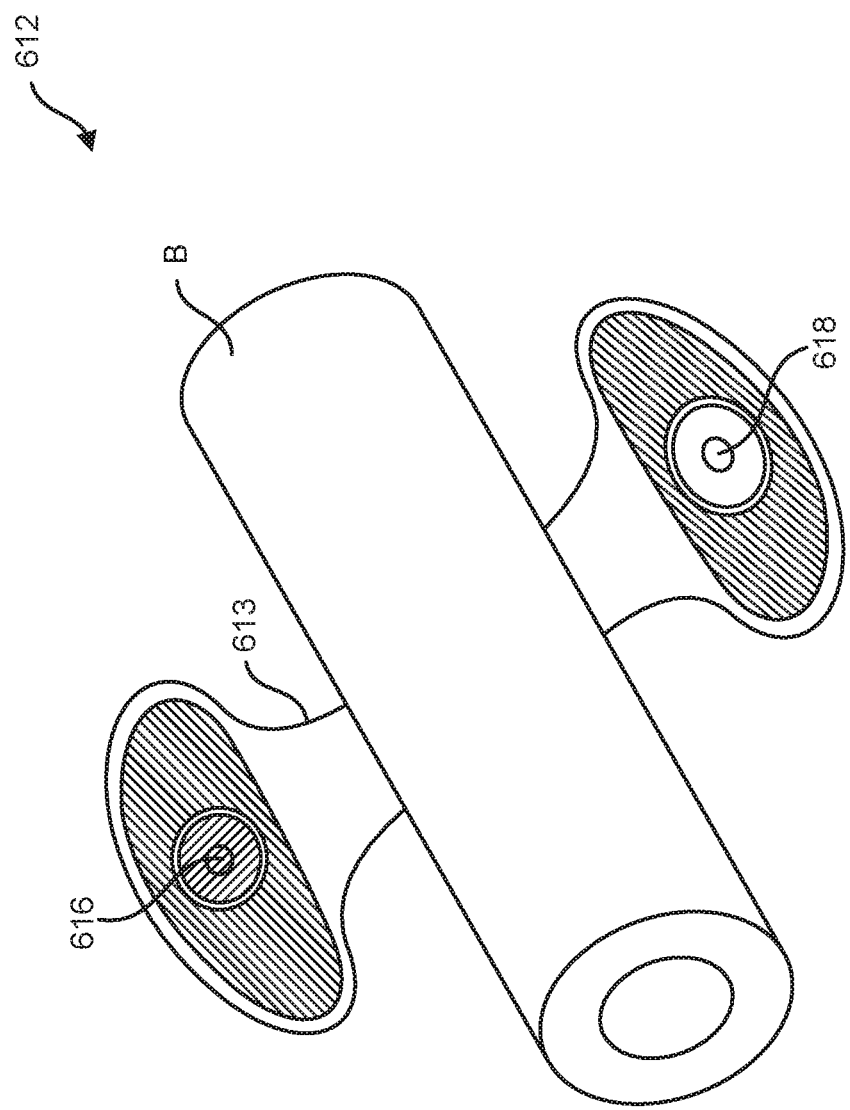
FIG. 13 is a perspective of the iontophoresis system of FIG. 11 partially wrapped around a body lumen of a patient illustrated schematically.

Referring to FIG. 13, in one or more embodiments, the body portion B is a body lumen such as a vein or an artery. The patch 612 is, therefore, sized and arranged for mounting active and indifferent electrodes 614, 616 in opposing relationship with respect to the body lumen. It will be understood that the patch 612 can be sized and arranged for use with other types of body portions (e.g., legs, arms, hands, fingers, toes, feet, etc.) in other embodiments. Moreover, it will be understood that other types of iontophoresis patches can be mounted on a body lumen (e.g., those configured to mount the active and indifferent electrodes in spaced apart relationship along the axis of the lumen) in other embodiments.

Figure 14:
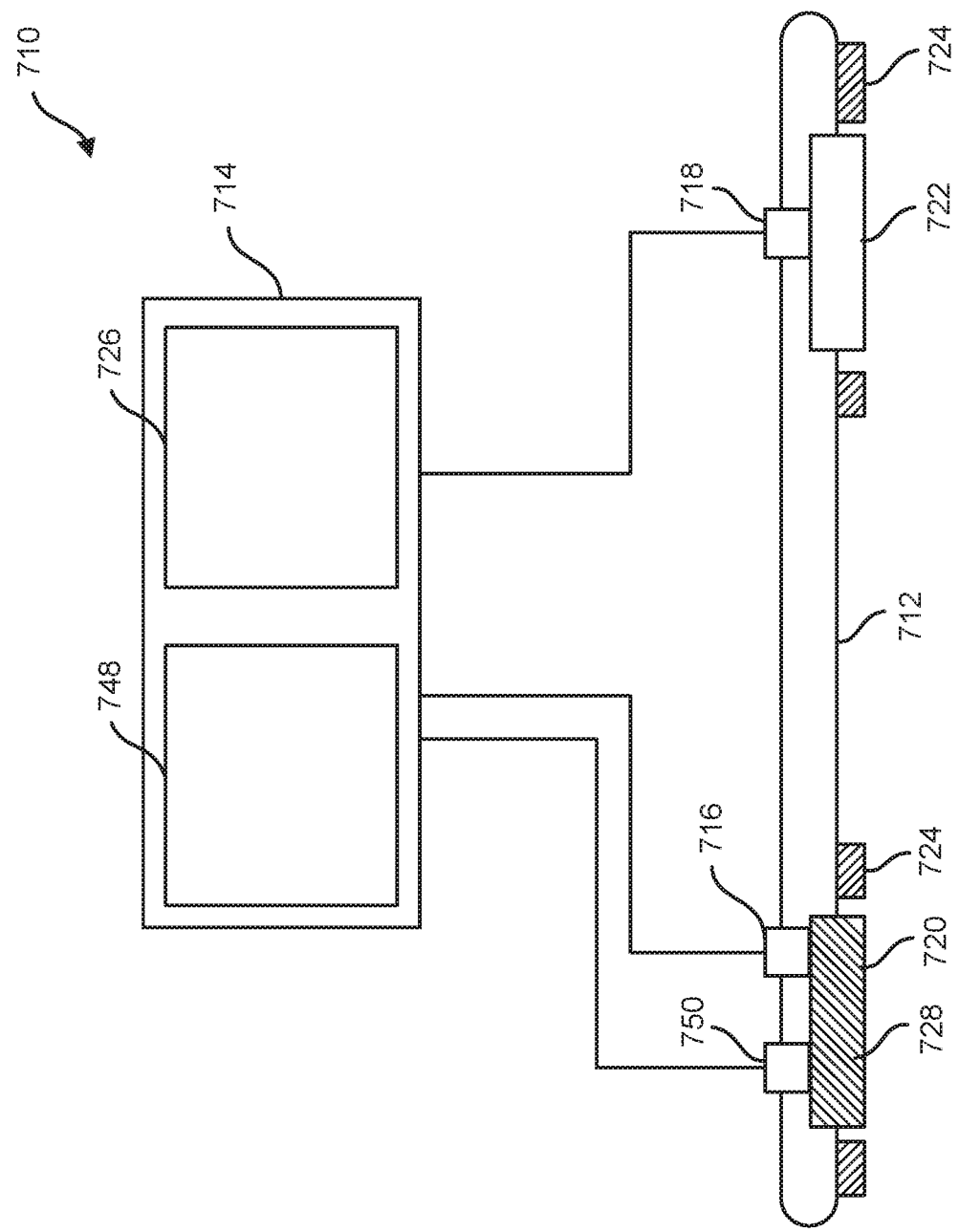
FIG. 14 is a schematic block diagram of another embodiment of an iontophoresis system.

Referring to FIG. 14, another embodiment of an iontophoresis system is generally indicated at 710. The iontophoresis system 710 includes a patch 712 that supports an active electrode 716 and an indifferent electrode 718. The patch 712 also supports an active electrode coupler 720 and an indifferent electrode coupler 722 configured to electrically couple the active electrode 716 and the indifferent electrode 718 to a body portion B when the patch is mounted on the body portion. The patch 712 further includes adhesive mounts 724 configured to mount the patch 712 on the body portion B so that each of the couplers 720, 722 are operatively connected to the body portion. The patch 712 supports a therapeutic agent reservoir 728 that can be preloaded with a therapeutic agent or filled with a therapeutic agent by a user. As discussed in further detail below, the patch 712 also supports one or more auxiliary devices 750 that are configured to be operatively connected to the body portion B of the patient and/or the reservoir 728 to enhance delivery of the therapeutic agent to the patient.

The illustrated iontophoresis system 710 includes an external electronics module 714, but the electronics module and other components of the system could be supported together by a single structure (e.g., a patch, a housing, etc.) in other embodiments. The electronics module 714 includes a power supply 726 and a controller 748. The controller 748 is configured to control the power supply 726 to selectively deliver power from the power supply to the electrodes 716, 718 to use the iontophoresis to deliver one or more doses of the therapeutic agent to the body portion B. In addition, the controller 748 is configured to be operatively connected to the auxiliary device 750 to control the operation of the auxiliary device. The power supply 726 is also operatively connected to the auxiliary device 750 to supply power to the auxiliary device in suitable embodiments.

In one exemplary embodiment, the auxiliary device 750 is a heater. For example, the auxiliary device 750 could be a resistive heater, an ultrasound generator, or any other suitable kind of heater. In one application, the heater can be operatively connected to the reservoir 728 to heat the therapeutic agent to a desired temperature. For example, the controller can be configured to operate the heater 750 to maintain the temperature of the therapeutic agent at the desired temperature. In addition, the controller 748 could be configured to prevent the system 710 from delivering electrical energy from the power supply 726 to the electrodes 716, 718 until after the therapeutic agent is heated to a desired temperature. In another embodiment, the heater 750 can be configured for operative connection with the body portion B of the patient when the patch 712 is mounted on the patient. The controller 748 can, for example, operate the heater 750 to increase the temperature of the body portion B above normal levels prior to and/or during iontophoresis. It is believed that increasing the temperature of the body portion B can widen pores or produce cavitation in the body portion and thereby increase the size and number of the pathways through which the therapeutic agent travels during use. Although the illustrated embodiment uses a controller 748 in a remote electronics module 714 to operate the heater 750 it will be understood that the heater could be subject to local control (e.g., using a local thermostat) without departing from the scope of the invention.

In another embodiment, the auxiliary device 750 includes a chiller. The chiller 750 can be operatively connected to one or both of the fluid reservoir 728 and the body portion B to decrease temperature. Suitably, the controller 748 can be operatively connected to the chiller 750 to operate the chiller to enhance delivery of the therapeutic agent to the body portion B or enhance the therapeutic effect of the agent in another way (e.g., by chilling the therapeutic agent to an active temperature). In one embodiment, the patch 712 supports both a heater and a chiller (e.g., a Peltier pump) that are operatively connected to the body portion B. In use, the controller 748 is suitably configured to cycle between heating the body portion B and cooling the body portion to open and close the pores in alternating fashion. It is thought that opening and closing pores may enhance a capillary action by which the therapeutic agent can be absorbed into the body portion B.

In still another embodiment, the auxiliary device 750 includes a vibrator. The vibrator can be operatively connected to the body portion B to vibrate the tissue. Suitably the controller 748 can be operatively connected to the vibrator 750 to operate the vibrator to enhance delivery of the therapeutic agent to the body portion B or enhance the therapeutic effect of the agent in another way (e.g., by agitating the therapeutic agent prior to use). For example, in one or more embodiments, the controller 748 is configured to selectively operate the vibrator 750 to vibrate the body portion B in order to work the therapeutic tissue deeper into the pores and/or shake loose matter that is obstructing the pores.

In yet another embodiment, the auxiliary device 750 is a magnetic field generator. The magnetic field generator 750 can be operatively connected to the body portion B to create a magnetic field in the tissue. The magnetic field generator 750 may be used with a magnetically charged therapeutic agent in a similar way to an iontophoresis system to drive the therapeutic agent into the body portion B. In suitable embodiments, the fluid reservoir 728 is filled with a therapeutic agent that has both an electrical charge and a magnetic charge so that the magnetic field generator 750 works in combination with the iontophoresis system 710 to drive the therapeutic agent into the body portion. In other embodiments, the fluid reservoir 728 contains at least a first therapeutic agent that has an electrical charge and a second therapeutic agent that has a magnetic charge. The iontophoresis system 710 drives the electrically charged therapeutic agent into the body portion B and the magnetic generator 750 drives the magnetically charged therapeutic agent into the body portion. In yet another embodiment, the therapeutic agent has only a magnetic charge. A magnetic generator can be used without iontophoresis to drive the therapeutic agent into the body portion. Suitably, the magnetic generator can be attached to a surface mount configured for mounting the generator on the body portion and operatively connected to a power supply that provides power. In addition, the magnetic generator is positioned relative a therapeutic agent reservoir to generate a magnetic field that passes through the reservoir and into the body portion. The reservoir can be preloaded or filled by a user with the magnetically charged therapeutic agent.

With continued reference to FIG. 14, in another embodiment, the auxiliary device is an acoustic energy generator. The acoustic energy generator can be an ultrasound generator or another acoustic energy generator configured to generate acoustic energy with a frequency of, for example, at least about 15 kHz. In a suitable embodiment, the ultrasound generator 750 is operatively connected to the body portion B to apply an ultrasound to the body portion. For example, an ultrasound gel may couple the acoustic energy generator 750 to the body portion B. In general, acoustic energy (e.g., focused ultrasound) can increase cavitation in tissue, and thus improve permeability for drug delivery. Acoustic energy can also aid in driving a therapeutic agent into tissue. For example, low intensity collimated beam ultrasound can increase blood flow to a treatment site and/or open pores of the subject. Moreover, focused ultrasound energy can be used to specifically target defined locations within the tissue in which to cause cavitation. By using the acoustic energy generator 750 to apply acoustic energy before, during, and/or after iontophoresis, delivery of the therapeutic agent is thought to be enhanced. In one aspect, the combination of acoustic energy from the auxiliary device 750 and iontophoresis from the system 710 is thought to enhance delivery by causing the drug to penetrate deeper into the tissue of the body portion B. In another aspect, the combination of acoustic energy from the auxiliary device 750 and iontophoresis from the system 710 is thought to enhance delivery by ensuring a larger percentage of the total applied therapeutic agent is delivered into the tissue of the body portion B.

The controller 748 can be configured to automatically sequence the operation of the acoustic energy generator 750 with the application iontophoresis to optimize delivery of the therapeutic agent. For example, in certain embodiments, the controller 748 is configured to cause the acoustic energy generator 750 to apply acoustic energy to the tissue of the body portion B before applying iontophoresis. In this way, the tissue is sonicated before the therapeutic agent is applied. In another embodiment, the controller 748 is configured to cause the acoustic energy generator 750 to apply acoustic energy to the tissue of the body portion B simultaneously with iontophoresis. In still another embodiment, the controller 748 is configured to cause the acoustic energy generator 750 to apply acoustic energy to the tissue of the body portion B after iontophoresis. This sequence may allow drug flow through the tissue to continue even after iontophoresis is complete. As discussed in further detail below, acoustic energy and iontophoresis may be sequenced so that the therapeutic agent need not be administered in an acoustic coupling gel, as with conventional sonophoresis techniques.

Although the auxiliary devices 750 discussed above were described in the context of an iontophoresis patch 710, it will be understood that they could be used alone or in combination in any of the iontophoresis systems 10, 110, 210, 310, 410, 510, 610 discussed above or additional systems discussed below.

Figure 15:
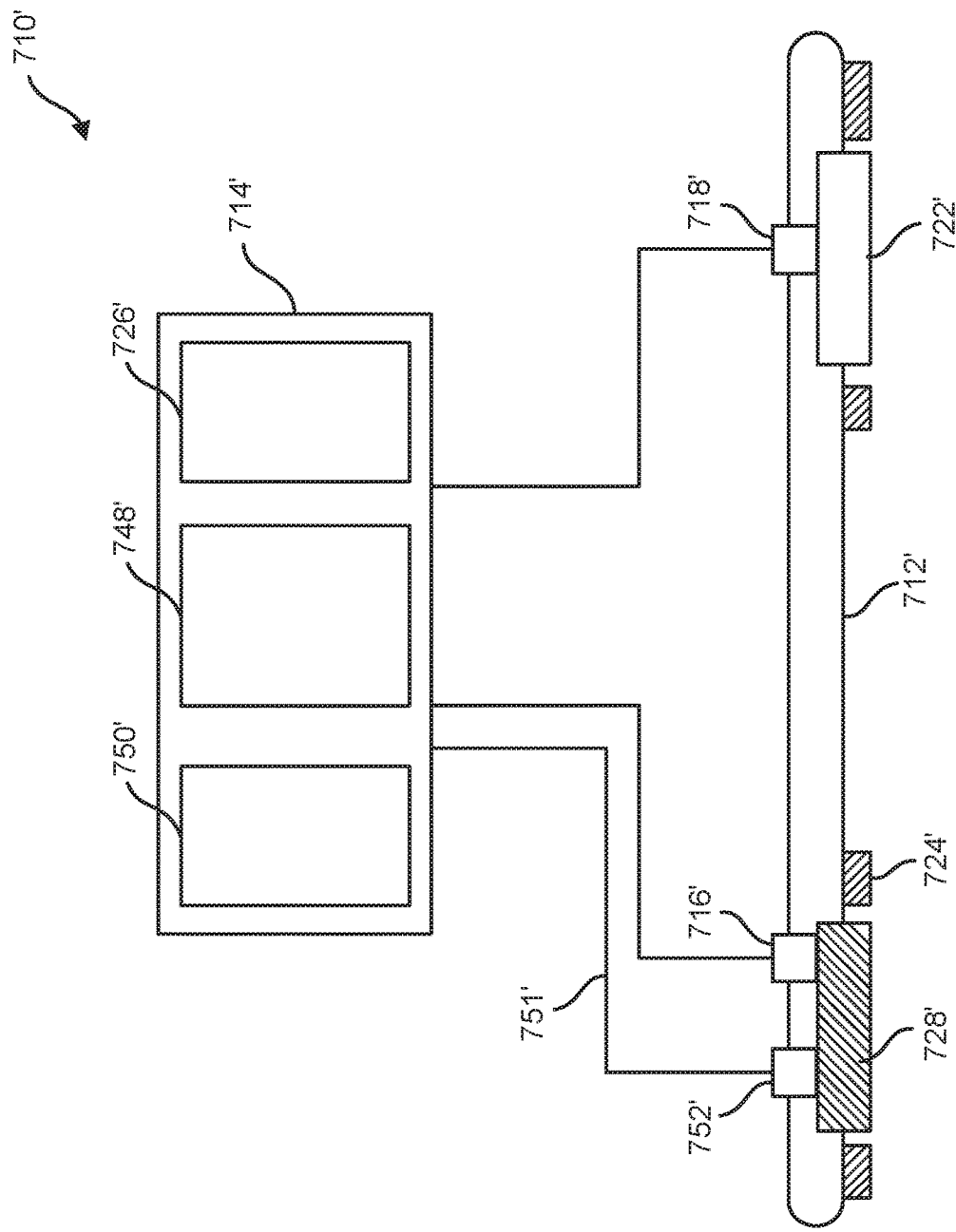
FIG. 15 is a schematic block diagram of another embodiment of an iontophoresis system.

Referring to FIG. 15, another iontophoresis system is generally indicated at 710'. The features of the iontophoresis system 712 given reference numbers above are given the same reference number in FIG. 15, followed by a prime symbol. The iontophoresis system 710' is substantially similar to the iontophoresis system 710, except for the differences noted hereinafter. Specifically, whereas the system 710 includes an auxiliary device 750 that is supported by the patch 712, an auxiliary device 750' of the system 710' is included in the external electronics module 714'. The system 710' includes an auxiliary input transmission line 751' that is configured to transmit the auxiliary input to an auxiliary input coupler 752' supported by the patch 712'. Thus, the auxiliary device 750' generates the auxiliary input and transmits the auxiliary input over the transmission line 751' to the coupler 752', which operatively couples the auxiliary input to the reservoir 728' and/or body portion B. Any suitable auxiliary device, such as the auxiliary devices 750 described above, may be used for the auxiliary device 750' in combination with a suitable coupler 752'.

Figure 16:
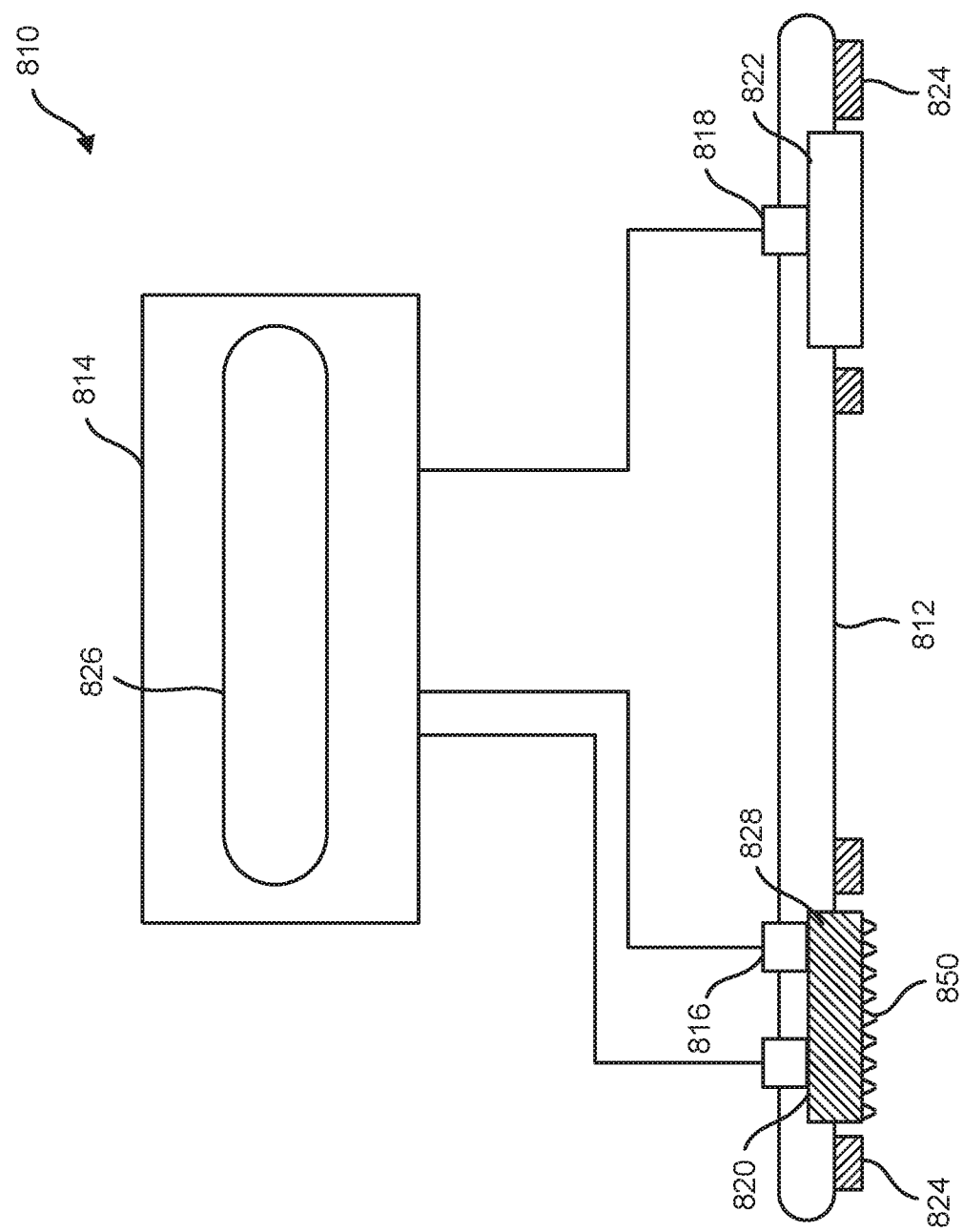
FIG. 16 is a schematic diagram of another embodiment of an iontophoresis system.

Referring to FIG. 16, another embodiment of an iontophoresis system is generally indicated at 810. The iontophoresis system 810 includes a patch 812 that supports an active electrode 816 and an indifferent electrode 818. The patch 812 also supports an active electrode coupler 820 and an indifferent electrode coupler 822. The patch 812 further includes adhesive mounts 824 configured to mount the patch 812 on the body portion B so that each of the couplers 820, 822 are operatively connected to the body portion. The patch 812 also supports a therapeutic agent reservoir 828 that can be preloaded with a therapeutic agent or filled with a therapeutic agent by a user. Like iontophoresis systems discussed above, the system 810 includes electronics 814, which can be mounted on the patch 812 or housed remotely, that include a power supply 826 for creating an electric field that drives iontophoresis.

The iontophoresis system 810 differs from the iontophoresis systems discussed above in that it includes a tissue-working structure 850 at the active electrode coupler 820. In general, a suitable tissue-working structure is configured to work the tissue of the body portion B (e.g., by abrading, puncturing, cutting, exfoliating, etc.) when the patch 812 is mounted on the body portion B to promote penetration of the therapeutic agent. In one or more suitable embodiments, the tissue-working structure includes an abrader, puncture member, cutter, and/or exfoliator, etc. The tissue-working structure 850 can be configured to work the tissue in the desired fashion by simply pressing the patch 812 onto the body portion B or by moving (e.g., rubbing) the patch across the body portion while the tissue-working structure contacts the target tissue. Although the tissue working structure 850 is described in the context of an iontophoresis patch 810, it will be understood that it could be used or alone or in combination in any of the iontophoresis systems 10, 110, 210, 310, 410, 510, 610, 710 discussed above or additional systems discussed below.

In one or more embodiments, a method of using an iontophoresis system comprises preparing target tissue of a body portion B before using iontophoresis to deliver a therapeutic agent to the target tissue. For example, any one or more of the following preparation techniques can be used alone or in combination: abrading, puncturing, cutting, exfoliating, removing hair, etc. The preparation technique(s) can be performed by a tissue-working structure 850 that is mounted on the iontophoresis system 810 or by another, separate device.

Figure 17:
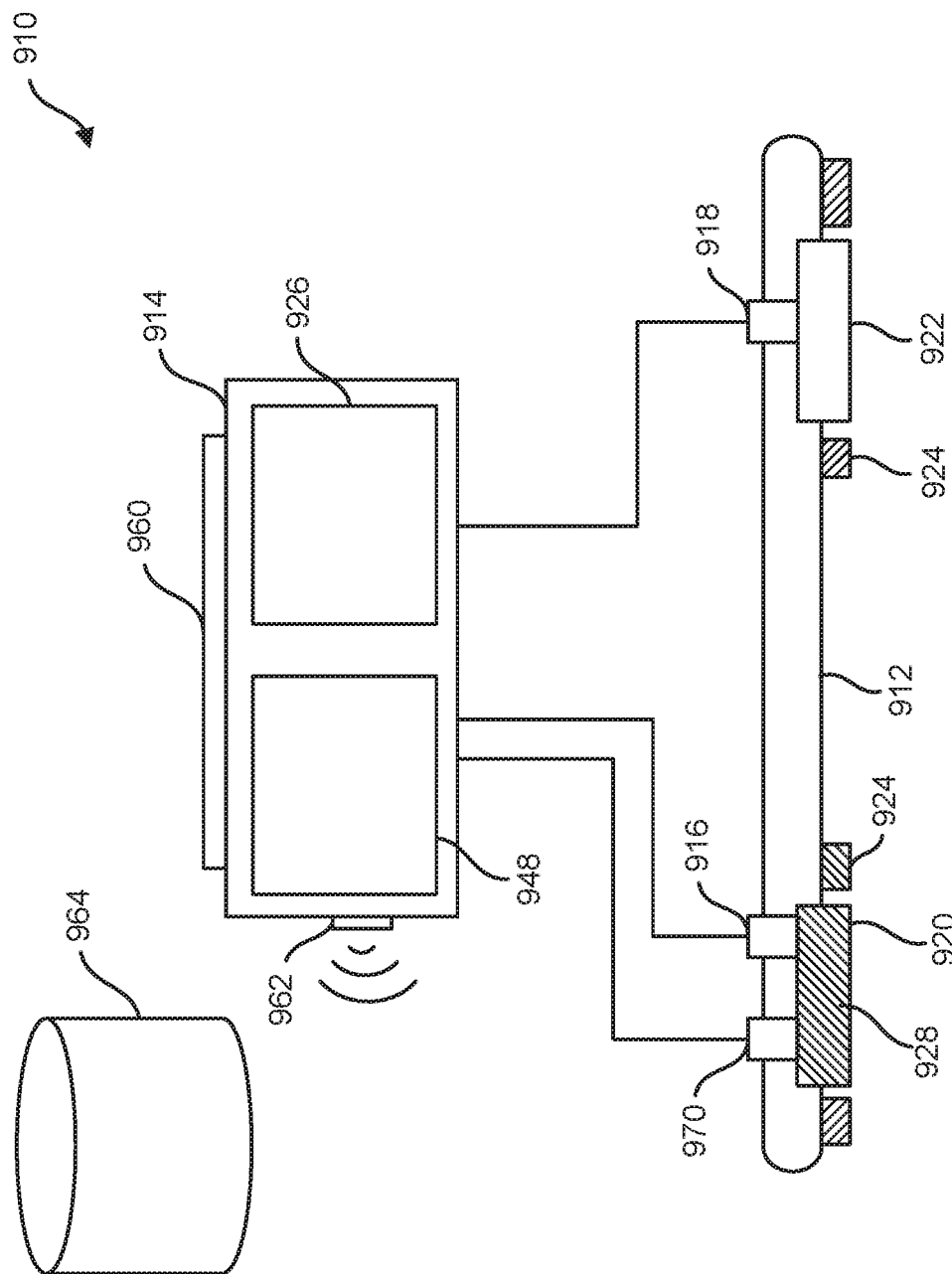
FIG. 17 is a schematic diagram of another embodiment of an iontophoresis system.

Referring to FIG. 17, another embodiment of an iontophoresis system is generally indicated at 910. The iontophoresis system 910 includes a patch 912 that supports an active electrode 916 and an indifferent electrode 918. The patch 912 also supports an active electrode coupler 920 and an indifferent electrode coupler 922. The patch 912 further includes adhesive mounts 924 configured to mount the patch 912 on the body portion B so that each of the couplers 920, 922 are operatively connected to the body portion. The patch 912 also supports a therapeutic agent reservoir 928 that can be preloaded with a therapeutic agent or filled with a therapeutic agent by a user. Like iontophoresis systems discussed above, the system 910 includes electronics 914 (which can be mounted on the patch 912 or housed remotely) that include a power supply 926 for creating an electric field that drives iontophoresis and a controller 948 for controlling the iontophoresis process. The electronics 914 further include a display 960 and a communications interface 962. The display 960 is configured to locally display information about the administration of the therapeutic agent to the user. The communications interface 962 operatively connects the electronics 914 to an external database 964 to provide data from the iontophoresis system 910 to the external database. In the illustrated embodiment, the communications interface 962 is a wireless interface, but hardwired interfaces may also be used in other embodiments. Although an external database 964 is shown, it will be understood that a database stored on a local memory of the electronics 914 may also be used.

The iontophoresis system 910 further includes at least one sensor 970. As discussed in further detail below, the sensor 970 can be operatively connected to one of the fluid reservoir 928 and body portion B to sense one or more parameters of the therapeutic agent, body portion, and/or iontophoresis process. Various types of sensors 970 can be used depending on the parameter to be sensed. Suitable parameters may, for example, include therapeutic agent temperature, body portion temperature, electrical field, magnetic field, radiation, therapeutic agent flow, etc.

In one or more embodiments, the sensor 970 is operatively connected to the controller 948 to provide a sensor signal representative of the sensed parameter to the controller. The controller 948 uses the sensor signal to control one or more aspects of the iontophoresis process. For example, in certain embodiments, the iontophoresis system 910 includes an auxiliary device (not shown). The controller 948 may be configured to receive the sensor signal from the sensor 970 and use it to control the operation of the auxiliary device. Likewise, the controller 948 may be configured to receive the sensor signal and use it to control the operation of the power supply 926.

In addition to the controller 948, the sensor 970 can also be operatively connected to one or both of the display 960 and the communications interface 962. The sensor 970 can suitably be operatively connected to the display 960 to render information about the sensor signal on the display. For example, if the sensor 970 is a temperature sensor, the display 960 may provide a real time display of the sensed temperature. If, as discussed in further detail below, the sensor 970 is configured to detect a parameter related to an amount of therapeutic agent that is successfully delivered, the display may provide a real time display of the amount of therapeutic agent delivered (e.g., as a percentage of a dose). The display 960 can also provide a visual indication when a complete dose has been delivered and the system 910 has been turned off. Audible indications may also be used in addition or as an alternative to visual indications. The sensor can, likewise, be operatively connected to the communications interface 962 to store the data from the sensor signal in the database 964. In one or more embodiments, the database 964 is a central database that is accessible by the patient's medical provider. The communications interface 962 can send data from the sensor 970 to the database 964 that relates to the patient's treatment using the iontophoresis system. This allows the medical provider to monitor a patient's progress in therapy. In certain embodiments, the medical provider can remotely alter a treatment protocol executed on the controller 948 based on the data the iontophoresis system 10 stores in the database. For example, if a patient is abusing the therapy, the medical provider could remotely adjust the treatment protocol to limit the amount of therapeutic agent that the system 910 delivers to the patient. The data may pass directly to the external database 964 using, for example, an internet connection, or the data may be first stored on a local memory and then uploaded to the database at a later time (e.g., when the patient returns to a medical office, etc.).

In one embodiment, the sensor 970 is configured to sense a parameter related to an amount of therapeutic agent delivered to the patient. The controller 948 receives the sensor signal and uses it to operate the power supply 926. For example, the controller 948 can automatically switch off the power supply 926 after it determines that an entire dose of the therapeutic agent has been delivered using the sensor signal. In one or more embodiments, the controller 948 instructs the communications interface 962 to store on the database 964 an indication of an amount of therapeutic agent delivered after each round of iontophoresis is complete. In certain embodiments, the controller 948 is in operative communication with the display 960 to provide information about an amount of therapeutic agent that has been delivered to the patient. The display 960 uses this information to, for example, generate a graphic indication representative of the progress in delivering a complete dose. In some embodiments, the controller 948 is operatively connected to an auxiliary device that is connected to the body portion B of the patient to affect the body portion in a way that enhances delivery of the therapeutic agent. The controller 948 uses the signal from the sensor 970 to selectively actuate the auxiliary device at times when the rate of delivery slows or stalls.

A suitable sensor 970 for sensing an amount of therapeutic agent delivered to a patient may include a Geiger counter. When the therapeutic agent is a radioactive substance such as certain chemotherapy drugs, a Geiger counter 970 may be used to measure radiation at the body portion B. The amount of detected radiation is thought to relate to the amount of radioactive drug delivered. Thus, the signal from the Geiger counter can be used to determine an amount of radioactive therapeutic agent that has been delivered.

Another suitable sensor 970 for sensing an amount of therapeutic agent delivered to a patient may include an optical sensor, such as a camera or scanner. In certain embodiments, a therapeutic agent can be optically labeled so that it is detectable using an optical sensor. The optical sensor provides a signal that includes an indication of a detected concentration of the optical label associated with the therapeutic agent. Thus, the optical signal can be used to determine an amount of radioactive therapeutic agent that has been delivered.

Another suitable sensor 970 for sensing an amount of therapeutic agent delivered to a patient may include an electrical charge sensor. As discussed above, the therapeutic agents used with the iontophoresis system 910 will suitably be ionic substances that are electrically charged. The electrical charge sensor can be configured to provide a signal that represents a sensed electric charge that is related to a detectable concentration of the therapeutic agent. Thus, the signal from the electrical charge sensor can be used to determine an amount of therapeutic agent that has been delivered.

The sensor 970 may also be used in combination with the controller 948 and an auxiliary device (not shown) to maintain certain parameters in the fluid reservoir 928. For example, when it is desirable to warm or cool the therapeutic agent in the reservoir 928 to a set point temperature prior to administration, the controller can receive a temperature signal from the sensor 970 representative of a temperature of the therapeutic agent and use the signal to control a heater and/or chiller that is operatively connected to the fluid reservoir. Likewise, when it is desirable to maintain the therapeutic agent in the reservoir 928 to a set point pH prior to administration, the controller can receive a pH signal from the sensor 970 representative of a pH of the therapeutic agent and use the signal to control a pH effector that is operatively connected to the fluid reservoir. In certain embodiments, the controller 948 may be further configured to prevent the power supply 926 from supplying current to the electrodes 916, 918 until the therapeutic agent in the reservoir 928 reaches the desired parameter(s).

In some embodiments, the sensor 970 can detect proper mounting of the patch 912 on the body portion B. For example, the sensor 970 may be a circuit detector configured to detect the presence of a completed circuit between the active electrode 916 and the indifferent electrode 918. The controller 948 can be configured to prevent the power supply 926 from supplying current to the electrodes 916, 918 until a circuit is detected. In some embodiments, the system 910 can be configured to a measure a resistance or impedance between the active electrode 916 and the indifferent electrode 918. The controller 948 may suitably be configured to prevent the power supply 926 from supplying current to the electrodes 916, 918 until the sensor shows that the resistance between the two electrodes is within a predetermined range that is associated with the electrical resistance of the body portion B.

Figure 18:
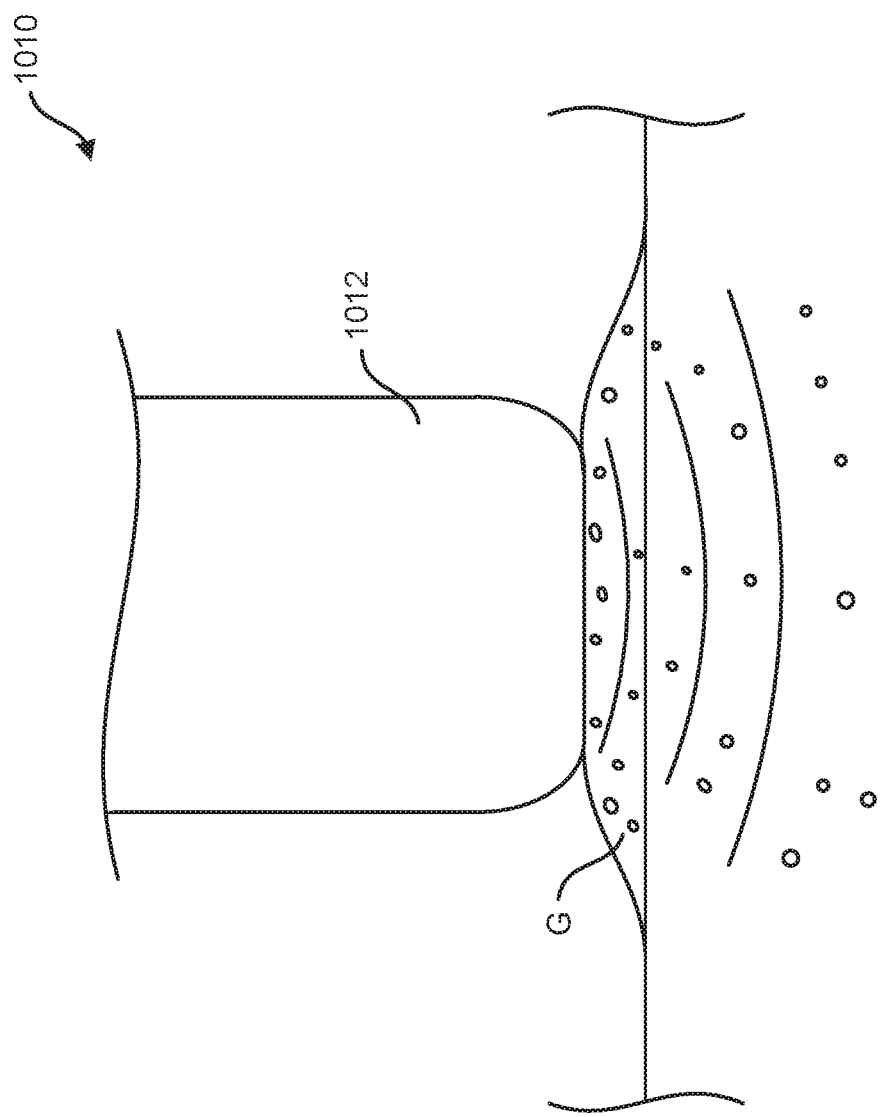
FIG. 18 is a schematic elevation of an acoustic system delivering a therapeutic agent to a body portion.

Referring to FIG. 18, an acoustic system for delivering a topical therapeutic agent to a body portion B is generally indicated at 1010. The acoustic system 1010 includes an acoustic energy generator 1012 that generates acoustic energy configured to enhance delivery of the topical therapeutic agent to the body portion B. The acoustic system 1010 is suitably configured to deliver the therapeutic agent to the body portion B using sonophoresis. In one or more embodiments, the acoustic energy generator 1012 is configured to generate acoustic energy having a frequency of at least about 15 kHz. In other embodiments, the acoustic energy generator 1012 is configured to generate acoustic energy having a frequency of from about 3 kHz to about 10 MHz (e.g., from about 20 kHz to about 1 MHz). In still other embodiments, the acoustic energy generator 1012 is configured to generate ultrasound energy. In the example illustrated in FIG. 18, a glycerin gel G acts as an acoustic coupler for operatively coupling the acoustic energy generator 1012 to the body portion B. The therapeutic agent is shown dispersed in the gel G to illustrate how the acoustic energy generator would be used in conventional sonophoresis. In use, the acoustic energy generator 1012 generates acoustic energy that enhances the permeability of the body portion B, causes cavitation, and/or causes diffusion of the therapeutic agent into the body portion (e.g., skin). The acoustic energy, therefore, enhances the delivery of the therapeutic agent into the body portion. However, some of the glycerin gel G is not able to be absorbed into the body portion B. As a result, some of the therapeutic agent remains suspended in the gel G and is not delivered to the patient.

To prevent a portion of the therapeutic agent from remaining suspended in unabsorbed gel G, the therapeutic agent may be applied to the body portion B separately from the gel. For example, in one method of using the acoustic system 1010, the therapeutic agent is applied to the body portion B before applying the gel and before applying the acoustic energy. In another method of using the acoustic system 1010, the therapeutic agent is applied to the body portion B after applying the gel and acoustic energy and removing the gel from the body portion. The therapeutic agent can be dissolved in a suitable topical solvent and applied directly to the body portion B (e.g., skin).

In suitable embodiments, the topical application of the therapeutic agent is further enhanced using iontophoresis. For example, an iontophoresis system, such as one having any of the features of the systems 10, 110, 210, 310, 410, 510, 610, 710, 810, 910 discussed above, can be used to deliver a therapeutic agent using enhanced iontophoresis before or after using the acoustic system 1010. Thus, the acoustic system 1010 is used to increase permeability of the body portion and/or further drive a therapeutic agent that is administered to a body portion B using iontophoresis. Suitably, the acoustic system 1010 can be used as an auxiliary device in an iontophoresis system. Optionally, a controller of the iontophoresis can control the sequencing of acoustic energy and iontophoresis to enhance delivery of a therapeutic agent to a patient. It will be understood that the acoustic system 1010 can also be used without iontophoresis.

When applied directly to the body portion B, the penetration of the therapeutic agent can be monitored. For example, when the therapeutic agent is applied to the body portion B before the acoustic energy, the user can monitor the absorption of the solvent into the skin (e.g., using the sensor 970 of the iontophoresis system 910) and refrain from applying acoustic energy until all of the solvent is determined to be absorbed. After all of the solvent appears to be absorbed, the user can apply acoustic energy to the body portion at the location where the therapeutic agent was applied to improve penetration. When the acoustic energy is applied to the body portion B before the therapeutic agent, the user can wipe away the acoustic coupling gel before applying the therapeutic agent. This prevents the therapeutic agent from becoming suspended in the gel. By applying the therapeutic agent after the acoustic energy has been applied, delivery is enhanced because the permeability of the body portion is increased by the acoustic energy.

It is believed that applying the acoustic energy through the acoustic coupling gel G at a separate time from the therapeutic agent results in more certainty about the dose of the therapeutic agent that is delivered to the patient. As a result, the above described method of administration can be used with dose-dependent and/or expensive therapeutic agents that are not well-suited for suspension in an acoustic coupling gel. Examples of suitable therapeutic agents for use with the methods of administration described above include, for example, chemotherapy drugs, Arnica, Voltaren, Morphine, salicylic acid, narcotics, chemotherapeutic agents, antiviral agents, RNA/DNA treatments, cannabidiol, etc.

In one application, a user sequences the use of acoustic energy and a wrinkle reducing agent to target skin of a patient. For example, after applying acoustic energy to the skin to increase permeability, a user can remove residual coupling gel from the target skin and apply water. Due to the increased porosity of the skin, the water deeply penetrates the skin to decrease wrinkles in the target area. Suitably, the target skin can be all or part of the face of a patient, which can be submersed in a water bath after application of acoustic energy. In certain embodiments, additional wrinkle reducing agent can be suspended in the acoustic coupling gel to be administered to the patient during the application of acoustic energy. As an alternative to applying water in a post-acoustic-treatment administration, water can be applied to the target skin before applying the acoustic energy. At least some of the pre-applied water enters the pores of the target skin. Then, when acoustic energy is applied to the target skin, it drives the retained water deeper into the skin to reduce wrinkles. In some wrinkle treatment applications, water can be supplemented or replaced with another wrinkle reducing agent such as, for example, a collagen, a cream, an enhancer, etc. It is also contemplated that water could be replaced or supplemented with Botox, for example, in a DMSO solution.

In another application, a user sequences the use of acoustic energy and a therapeutic agent for the treatment of psoriasis. A suitable therapeutic agent is applied directly (e.g., without interference from an acoustic coupling gel) to the body part that suffers from psoriatic lesions in alternating fashion with acoustic energy (e.g., before or after applying the acoustic energy). In one or more embodiments, the psoriatic therapeutic agent is at least one of water, a chemotherapeutic agent, an RNA/DNA treatment, etc. By sequencing the application of acoustic energy and therapeutic agent, psoriatic treatments can be delivered topically, without an IV.

Basal cell cancers or other cancers such as melanoma could also be treated using these sequencing techniques. A suitable therapeutic agent for treating cancer, such as a chemotherapy drug, is applied directly to the body part where the cancer is located in alternating fashion with acoustic energy.

In still another application, a user can apply a surgical marker to target tissue using the sequencing technique. A suitable surgical marker is applied directly to the body part that includes the target tissue in an alternating fashion with acoustic energy. A surgeon can subsequently use the marker to identify tissue for, for example, resection.

In another application, a user can sequence acoustic energy with a therapeutic agent to treat Dupuytren's contracture. For example, a therapeutic agent such as Collagenous is applied to the affected skin in alternating fashion with acoustic energy. Since Collagenous is very expensive, it can be applied to the bare skin for, for example from about 30 seconds to about 5 minutes to ensure administration of a complete dose.

In yet another application, a user can sequence acoustic energy with negative pressure wound treatment to treat a wound, such as a diabetic ulcer or other chronic wound. For example, a therapeutic agent may be combined with negative pressure therapy in alternating fashion with acoustic energy. In one or more embodiments, the negative pressure therapy and therapeutic agent are combined using the iontophoresis system 410 as discussed above and applied in alternating fashion with the acoustic energy from the acoustic energy generator 1010.

In certain applications, a user can sequence focused acoustic energy on a specific location of skin to generate localized permeability that allows a therapeutic agent to pass transdermally through the skin and into a bodily lumen or organ. For example, a therapeutic agent can be applied to the targeted area of the skin above a blood vessel in alternating fashion with focused acoustic energy to deliver the therapeutic agent to the blood stream without an injection.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. An iontophoresis system for delivering a therapeutic agent to a subject, the iontophoresis system comprising:
   a flexible patch support configured to be positioned over a wound on a body portion of a subject and create an airtight seal;
   an active electrode and an indifferent electrode configured to be connected to the support and configured to be in electrical communication with one another through the body portion of the subject, the active electrode configured to be selectively coupled to a power supply to generate a current extending through the body portion between the active electrode and the indifferent electrode;
   a controller configured to be operatively connected to the active electrode and the power supply to control an amount of power transmitted from the power supply to the active electrode to generate the current through the body portion;
   a vacuum source operatively connected to an air fitting configured to extend through the flexible patch support, wherein the vacuum source is configured to apply a negative pressure between the flexible patch support and the wound on the body portion of the subject;
   a fluid reservoir preloaded with a therapeutic agent and configured to be connected to the support in operative alignment with the active electrode for delivering the therapeutic agent from an outlet of the fluid reservoir into the body portion of the subject using an electromotive force of the current passing through the body portion; and
   a removable cover covering at least the outlet of the reservoir to contain the therapeutic agent within the fluid reservoir until the cover is removed from the outlet,
   wherein the wound on the body portion of the subject is at least one of a diabetic ulcer and a chronic wound.

2. An iontophoresis system as set forth in claim 1, further comprising a sensor coupled to the controller, the sensor configured to measure a sufficient negative pressure between the flexible patch support and the wound on the body portion of the subject, and the controller configured to activate the power supply to transmit power to the active electrode when the negative pressure measured by the sensor reaches a predetermined threshold.

3. An iontophoresis system as set forth in claim 2, wherein the cover comprises a peel strip extending over the distal end of the support.

4. An iontophoresis system as set forth in claim 1, further comprising: a reusable module including the support; and a disposable module including the reservoir and the cover, the disposable module being configured to be selectively connected to the reusable module.

5. An iontophoresis system as set forth in claim 4, wherein at least one of the reusable module and the disposable module comprises a mounting structure for mounting said one of the reusable module and the disposable module on the other of the reusable module and the disposable module.

6. An iontophoresis system as set forth in claim 4, wherein the disposable module includes the active electrode.

7. An iontophoresis system as set forth in claim 4, wherein the reusable module includes the indifferent electrode.

8. An iontophoresis system as set forth in claim 7, wherein the reusable module includes the active electrode.

9. An iontophoresis system as set forth in claim 1, wherein the reservoir and the active electrode are each fastened to the support, the iontophoresis system further comprising a removable release strip separating the reservoir and the active electrode.

10. An iontophoresis system as set forth in claim 1, wherein the reservoir comprises an absorbent structure impregnated with the therapeutic agent.

11. An iontophoresis system as set forth in claim 10, wherein the absorbent structure defines one or more passages configured for directing the therapeutic agent toward the body portion through capillary flow.

12. An iontophoresis system as set forth in claim 1, further comprising system electronics coupled to the controller, the system electronics configured to measure an impedance of the body portion of the subject, and the controller configured to activate the power supply to transmit power to the active electrode when the impedance of the body portion reaches a predetermined threshold.

13. An iontophoresis system as set forth in claim 1, further comprising a mount configured to mount the support on the body portion of the subject such that the therapeutic agent reservoir connected to the support is operatively connected to the body portion for delivering the therapeutic agent into the body portion.

14. An iontophoresis system as set forth in claim 1, wherein the controller is configured to prevent the active electrode from drawing power from the power supply after a predetermined amount of time.

15. An iontophoresis system as set forth in claim 1, further comprising an auxiliary device configured to generate an auxiliary input transmissible to the body portion of the subject, the controller being operatively connected to the auxiliary device to control the auxiliary device.

16. An iontophoresis system as set forth in claim 15, wherein the auxiliary device comprises one of a heater, a chiller, a vibrator, a magnetic field generator, and an acoustic energy generator.

17. An iontophoresis system as set forth in claim 1, further comprising a tissue working structure connected to the reservoir and configured to work the tissue of the body portion by one of abrading, puncturing, cutting, and exfoliating the tissue.

18. An iontophoresis system as set forth in claim 1, further comprising a sensor configured to sense one or more parameters of the therapeutic agent, the body portion of the subject, and a treatment being administered by the iontophoresis system and to transmit a signal representative of the sensed parameter to the controller.

19. An iontophoresis system as set forth in claim 18, wherein the controller is configured to receive the signal and use the signal to control the amount of power from the power supply transmitted to the active electrode.

20. A method of delivering a therapeutic agent to a body portion of a subject, the method comprising:
   removing a cover of an iontophoresis system extending over an outlet of a reservoir preloaded with a therapeutic agent;
   engaging, after said removing a cover, the iontophoresis system with the body portion of the subject so that the reservoir is operatively aligned with the body portion; and
   using a controller to convey power from a power supply to an active electrode of the iontophoresis system to draw a current through the body portion of the subject and deliver the preloaded therapeutic agent from the reservoir through the outlet and into the body portion of the subject using an electromotive force of the current,
   wherein the body portion of the subject is at least one of a diabetic ulcer and a chronic wound.

* * * * *